Figure 1:
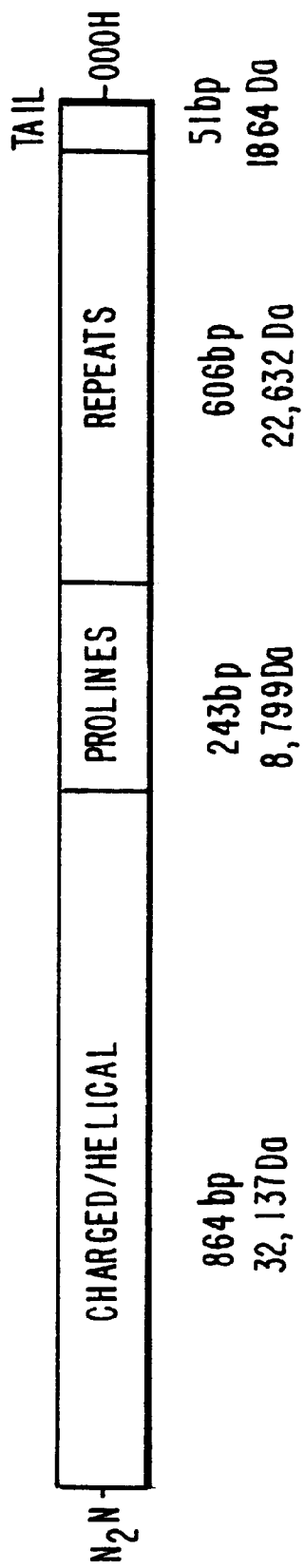

United States Patent [19]

Briles et al.

[11] Patent Number: 5,965,400

[45] Date of Patent: *Oct. 12, 1999

[54] DNA ENCODING A TRUNCATED PNEUMOGOCCAL SURFACE PROTEIN (PSPA)

[75] Inventors: David E. Briles; Janet L. Yother, both of Birmingham, Ala.

[73] Assignee: UAB Research Foundation, Birmingham, Ala.

[*] Notice: This patent is subject to a terminal disclaimer.

[21] Appl. No.: 08/247,491

[22] Filed: May 23, 1994

Related U.S. Application Data

[63] Continuation of application No. 07/835,698, Feb. 12, 1992, abandoned, which is a continuation-in-part of application No. 07/656,773, Feb. 15, 1991, abandoned.

[51] Int. Cl.[6] .............................. C12P 21/02; C12N 1/21; C12N 15/31; C07K 1/18

[52] U.S. Cl. ................ 435/69.3; 435/252.3; 435/252.33; 435/253.1; 435/253.4; 435/849; 435/885; 530/416; 530/417; 536/23.7

[58] Field of Search ............................. 435/253.4, 253.1, 435/69.3, 252.33, 252.3, 849, 885; 536/23.7; 530/416, 417

[56] References Cited

U.S. PATENT DOCUMENTS

| | | |
|---|---|---|
| 4,496,538 | 1/1985 | Gordon . |
| 4,673,574 | 6/1987 | Anderson . |

OTHER PUBLICATIONS

Growth Characteristics of Group A Streptococci in a New Chemically Defined Medium, Rijn et al—Inf. and Imm. Feb. 1980, pp. 444–448.

McDaniel et al. 1989. Abstracts of the 89th annual meeting of the ASM, Abstract D–255.
Stover et al. Nature (351):456–60 Jun. 1991.
McDaniel et al (I), J.Exp.Med. 160:386–397, 1984.
McDaniel et al (II), Microbial Pathogenesis 1:519–531, 1986.
McDaniel et al (III), J.Exp.Med. 165:381–394, 1987.
McDaniel et al (IV), Infect. Immun., 59:222–228, 1991.
Crain et al, Infect.Immun., 58:3293–3299, 1990.
Abstracts of 89th Annual Meeting of the American Society for Microbiology, p. 125, item D–257, May 1989.
Abstracts of 90th Annual Meeting of the American Society for Microbiology, p. 98, item D–106, May 1990.
Abstracts of 3rd International ASM Conference on Streptococcal Genetics, p. 11, item 12, Jun. 1990.
Talkington et al, Infect. Immun. 59:1285–1289, 1991.
Yother et al, J. Bacteriol. 174:601–609, 1992.
Yother et al, J. Bacteriol. 174:610–618, 1992.
Bowie et al. Science 247:1306 1990.
Kumar et al PNAS 87:1337–1341 1990.
Sambrook et al. "Molecular Cloning, A Laboratory Manual" 1989 see Chapter 13.
Young and Davis PNAS 80:1194–98 Mar. 1983.

*Primary Examiner*—Anthony C. Caputa
*Attorney, Agent, or Firm*—Curtis, Morris & Safford P.C.

[57] ABSTRACT

A purified pneumococcal surface protein A (PspA) comprises a truncated form of the PspA protein which is immunoprotective and contains the protective epitopes of PspA. The PspA protein is soluble in physiologic solution and lacks at least the cell membrane anchor region of the whole protein. The protein is formed by insertion-duplication of mutagenesis of *S. pneumoniae* with pspA gene and expression of the truncated protein into the growth medium.

13 Claims, 10 Drawing Sheets

DOMAINS OF THE MATURE PspA

```
                            a    b    c    d    e    f    9
GLU GLU ser pro val ala ser gin  ser  LYS  ala  GLU  LYS  ASP  14
                            tyr  ASP  ala  ala  LYS  LYS  ASP  21
                            ala  LYS  asn  ala  LYS  LYS  ala  28
                            val  GLU  ASP  ala  gin  LYS  ala  35
                            leu  ASP  ASP  ala  LYS  ala  ala  42
                            gin  LYS  LYS                      45
```

FIG. 2

FIG. 3B

```
481/ GCC GCA AAA GAC GCA GCA GAT AAG ATG ATA  511/ AAG AAA CGC GAA GAG GCA    FIRST 45 aa,
     ala ala lys asp ala ala asp lys met ile       lys lys arg glu glu ala    BEGINNING WITH
161/                                          /171                             glu, ARE SAME
                                                                               AS FOUND BY aa
541/ AAA ACT AAA TTT AAT ACT GTT CGA GCA ATG  571/ GAG CCA GAG CAG TTC GCT    SEQUENCING
     lys thr lys phe asn thr val arg ala met       glu pro glu gln leu ala    (TALKINGTON
181/                                          /191                             ETC.
601/ ACT AAG AAA TCA GAA GAA GCT AAA CAA GCA  631/ CCA GAA GCA AAA CTA GAA
     thr lys lys ser glu glu ala lys gln ala       pro glu ala lys leu glu
201/                                          /211
661/ AAG GCT AAA AAA TTA AAA GAG GCT AAA CAA  691/ GCA GCA AAA CAA AAA CTA
     lys ala lys lys leu lys glu ala lys gln       ala ala lys gln lys leu
221/                                          /231
721/ GAA GCT GAA GTC GTC CCT CAA GCT AAA CCT  751/ AAA AAA TTG AAA GCC AAA
     glu ala glu val val pro gln ala lys pro       lys lys leu lys ala lys
241/                                          /251
781/ GAT GCT GAG CTC CTC GAG ATT GAT CAA CCT  811/ ATC ATC ATC ATC GAG CAT    α-HELICAL,
     asp ala glu leu leu glu ile asp gln pro       ile ile ile ile glu his    CHARGED
                                                                               DOMAIN
261/                                          /271
841/ CTA GAA CAG CCT CTT CTT TCT TGG AAA ATT  871/ GCC TCT GAT TAT CTA TCA
     leu glu gln pro leu leu ser trp lys ile       ala ser asp tyr leu ser
281/                                          /291
901/ TTC CGT GCT GAT AAG ATT GAT GAG TTA GAC  931/ AAA TAT AAA TTG GAT GAT
     phe arg ala asp lys ile asp glu leu asp       lys tyr lys leu asp asp
301/                                          /311
961/ GAG TTA AGT GAT AAG ATT ATC GAC AAG TTA  991/ AAT ATT GCA ATT TTG GCA
     glu leu ser asp lys ile ile asp lys leu       asn ile ala ile leu ala
321/                                          /331
     AAA GCT GCT GAA GAC AAT GTA GAA TAC TTT       GAA GGT TTA GAG AAA ACT
     lys ala ala glu asp asn val glu tyr phe       glu gly leu glu lys thr
```

FIG. 3C

```
1021/                                                    1051/          351
ATT GCT GCT AAA AAA GCT GAA TTA GAA AAA ACT GAA GCT GAC CTT AAG AAA GCA GTT AAT
ile ala ala lys lys ala glu leu glu lys thr glu ala asp leu lys lys ala val asn
     1081/                              361
GAG CCA GAA AAA CCA GAA CCA GCT CCA GCT CCA GAA ACT CCA GCC CCA.GAA GCA CCA GCT GAA CAA
glu pro glu lys pro glu pro ala pro ala pro glu thr pro ala pro glu ala pro glu gln
     1141/                              381
CCA AAA CCA GCG CCG CCT CAA CCA GCT CCC GCA CCA AAA CCA GAG AAG CCA GCT GAA
pro lys pro ala pro pro gln pro ala pro ala pro lys pro glu lys pro ala glu
     1201/                              401
CAA CCA AAA CCA GAA AAA ACA GAT CAA GCT GAT CAA ACT GCT CGT AGA TCA
gln pro lys pro glu lys thr asp gln ala asp glu ala glu tyr ala arg arg ser
     1261/                              421                                        PROLINE-RICH DOMAIN
GAA GAA GAA TAT AAT CGC TTG ACT CAA CAG CAA CCA AAA GCT GAA AAA CCA GCT CCT
glu glu glu tyr asn arg leu thr gln gln gln pro lys ala glu lys pro ala pro
     1321/                              441                1351/
GCA CCA AAA ACA GGC TGG AAA CAA AAC AAC GGT ATG TGG TAC TTC TAC AAT ACT GAT GGT
ala pro lys thr gly trp lys gln asn asn gly met trp tyr phe tyr asn thr asp gly
     1381/                              461                1411/          471
TCA ATG GCG ACA GGA TGG CTC CAA AAC AAC TGG TCA TAC CTC AAC AGC AAT GGT
ser met ala thr gly trp leu gln asn asn trp ser tyr leu asn ser asn gly
     1441/                              481                1471/          491       PROLINES
GCT ATG ACA GCT ACA GGT TGG CTC CAA TAC AAT TAC TGG TCA TAC CTC AAC AAC GGC
ala met thr ala thr gly trp leu gln tyr asn tyr trp ser tyr leu asn asn gly
     1501/                              501                1531/          511
GCT ATG GCA ACA GCT ACA GGT TGG GCT AAA GTC AAA TAC TGG TCA TAC CTC AAC AAT GGT
ala met ala thr ala thr gly trp ala lys val lys tyr trp ser tyr leu asn asn gly
     1561/                              521                1591/          531
GCT ATG GCT ACA GCT ACA GGT TGG CTC CAA TAC TAC TGG TCA TAT CTC AAC AAC GGC
ala met ala thr ala thr gly trp leu gln tyr tyr trp ser tyr leu asn asn gly
```

FIG. 3D

| | | | | | | | | | | | | REPEAT DOMAIN |
|---|---|---|---|---|---|---|---|---|---|---|---|---|
| 1621 / 541 | | | | | | | 1651 / 551 | | | | | |
| GCT ala | ATG met | GCA ala | ACA thr | GGT gly | TGG trp | GCT ala | AAA lys | GTC val | AAC asn | GGT gly | TCA ser | TAC tyr | TAC tyr | CTC leu | AAC asn | GCT ala | AAT asn | GGT gly |
| 1681 / 561 | | | | | | | 1711 / 571 | | | | | |
| GCT ala | ATG met | GCT ala | ACA thr | GGT gly | TGG trp | CTC leu | CAA gln | TAC tyr | AAC asn | GGT gly | TCA ser | TAC tyr | TAC tyr | CTC leu | AAC asn | GCT ala | AAC asn | GGT gly |
| 1741 / 581 | | | | | | | 1771 / 591 | | | | | |
| GCT ala | ATG met | GCT ala | ACA thr | GGT gly | TGG trp | GCT ala | AAA lys | GTC val | AAC asn | GGT gly | TCA ser | TAC tyr | TAC tyr | CTC leu | AAC asn | GCT ala | AAT asn | GGT gly |
| 1801 / 601 | | | | | | | 1831 / 611 | | | | | |
| GCT ala | ATG met | GCA ala | ACA thr | GGT gly | TGG trp | GTG val | AAA lys | GAT asp | GGA gly | GAT asp | ACC thr | TAT tyr | CTT leu | GAA glu | GCA ala | TCA ser | GGT gly |
| 1861 / 621 | | | | | | | 1891 / 631 | | | | | |
| GCT ala | ATG met | AAA lys | GCA ala | AGC ser | CAA gln | TGG trp | TTC phe | AAA lys | GTA val | TCA ser | GAT asp | TGG trp | TAC tyr | TAT tyr | GTC val | AAT asn | GGT gly | TTA leu |
| 1921 / 641 | | | | | | | 1951 / 651 | | | | | |
| GGT gly | GCC ala | CTT leu | GCA ala | GTC val | AAC asn | ACA thr | ACT thr | GTA val | GAT asp | GCC ala | TAT tyr | AAA lys | TTG leu | ACA thr | TTT phe | GCC ala | AAT asn | GGT gly | GAA glu | TGG trp |
| 1981 / 661 | | | | | | | 2011 / 671 | | | | | |
| GGT gly | GCC ala | GAT asp | TAA OCH | ATT ile | AAA lys | GCA ala | TCT cys | TAA OCH | GAA glu | CAT his | TTG leu | ACA thr | TTT phe | TAA OCH | TTT phe | TGA OPA | AAC asn | AAA lys |
| 2041 / 681 | | | | | | | 2071 / 691 | | | | | |
| GTT val | TAA OCH | GCC ala | ala asp | TTG leu | AAT asn | AGA arg | TTT phe | ATG met | TTC phe | GTA val | TTC phe | TTT phe | AGG arg | TAC tyr | TAA OCH | | | |
| GAT asp | AAG lys | GTT val | CGA arg | TTG leu | AAT asn | AGA arg | TTT phe | ATG met | TTC phe | val | phe | met | arg | phe | phe | | | |

TRANSLATION STOP (END) IS AT TAA OCH

TAIL

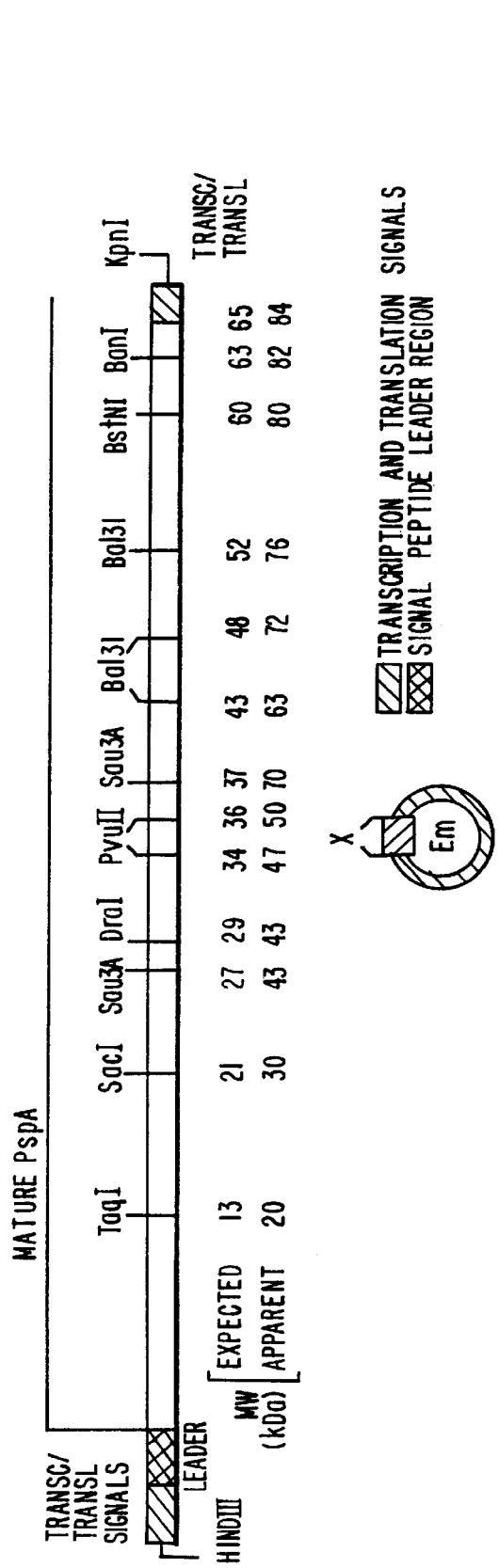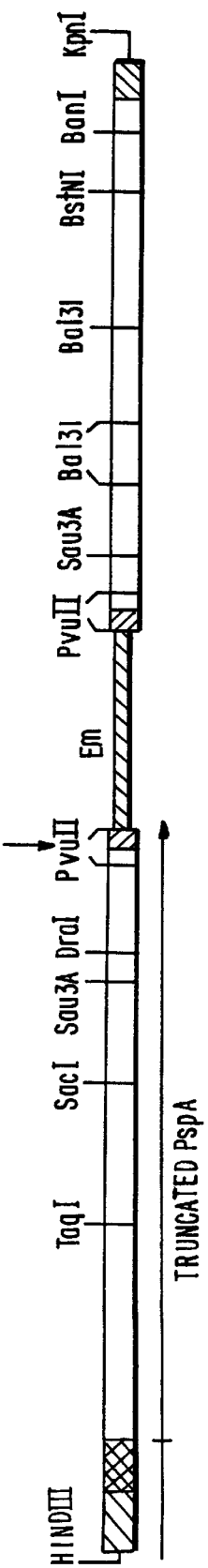
FIG. 4A
FIG. 4B

FIG. 5

|  |  |  | a | b | c | d | e | f | g |
|---|---|---|---|---|---|---|---|---|---|
|  |  | 1 | E | E | s | p | v | a | s |
|  |  | 8 | Q | s |  |  |  |  |  |
|  |  | 15 | y | D | K | a | E | K | D |
|  |  | 22 | a | K | N | a | K | K | D |
|  |  | 29 | v | E | D | a | Q | K | a |
|  |  | 36 | L | D | D | a | K | a | a |
| XI1526* |  | 43 | Q | K | K | y | D | E | D |
| XI126* |  | 50 | Q | K | K | t | E | E | K |
| XIR35 |  | 57 | a | a | l | E | K | a | a |
| XIR148 |  | 64 | s | E | E | m | D | K | a |
| XIR1224 |  | 71 | v | a | a | v | Q | Q | a |
|  |  | 78 | y | L | a | y | Q | Q | a |
|  |  | 85 | t | D | K | a | a | K | D |
|  |  | 92 | a |  |  |  |  |  |  |
|  |  |  |  |  |  | a | D | K | m |
|  |  | 97 | L | D | E | a | K | K | R |
|  |  | 104 | E | E | E | a | K | t | R |
|  |  | 111 | L | N | t | v | R | a | m |
|  |  | 118 | v | v | p | E | p | E | Q |
|  |  | 125 | L | a | E | t | K | K | K |
|  | 138 HHHHH | 132 | s | E | E | a | K | Q | K |
|  |  | 139 | a | p | E | L | t | K | K |
|  |  | 146 | L | E | E | a | a | K | K |
|  |  | 153 | L | E | E | a | E | K | K |
|  |  | 160 | a | t | E | a | K | Q | K |
| XIR16 |  | 167 | v | D |  |  |  |  |  |
|  |  |  |  |  | a | E | E | v | a |
|  |  | 174 | p | Q | a |  |  |  |  |
|  |  | 178 | L | a | E | L | E | N | K |
|  |  | 185 | v | H | R | L | E | Q | Q |
|  | 193 HHHHH | 192 | L | K | E | L | D | E | E |
|  |  | 199 | E |  |  |  |  |  | s |
|  |  |  |  |  |  | s | E | D | y |
|  |  | 204 | a | K | E | g | L | R | a |
|  |  | 211 | p | L | Q | s | K | L | D |
| XI64* |  | 218 | a | K | K | a | K | L | D |
| XIR278* |  | 225 | K |  |  |  |  |  | s |
| XI1325* |  | 226 | L | E | E | L | s | D | K |
|  |  | 233 | L | D | E | L | D | a | E |
|  |  | 240 | L | a | K | L | E | D | Q |
|  |  | 247 | L | K | a | a | E | E | N |
|  |  | 254 |  | N | N | v | E | D | y |
|  | 261 HHHHH | 260 | L | K | E | g | L | E | K |
|  |  | 267 | t | L | a | a | K | K | a |
| XI1323* |  | 274 | E |  |  |  |  |  |  |
|  |  | 275 | L | E | K | t | E | a | D |
|  |  | 282 | L | K | K | a | v | N | E |

FIG.6

| | Xi 126 | XiR 1224 | XiR 148 | XiR 1526 | XiR 35 | XiR 16 | XiR 278 | XiR 1325 | Xi 64 | XiR 1325 |
|---|---|---|---|---|---|---|---|---|---|---|
| KSD 1014 | ‡ | ‡ | ‡ | ‡ | ‡ | ‡ | ‡ | ‡ | ‡ | ‡ |
| JY 4306 | ‡ | ‡ | ‡ | ‡ | ‡ | ‡ | + | ‡ | ‡ | ‡ |
| JY 4310 | ‡ | + | ‡ | ‡ | ‡ | ‡ | – | – | – | – |
| JY 4285 | ‡ | + | – | ‡ | ‡ | + | – | – | – | – |
| KSD 1500 | – | – | – | – | – | – | – | – | – | – |
| BC 100 | – | – | – | – | – | – | ‡ | ‡ | ‡ | ‡ |
| BC 207 | – | – | – | – | – | + | ‡ | ‡ | ‡ | ‡ |

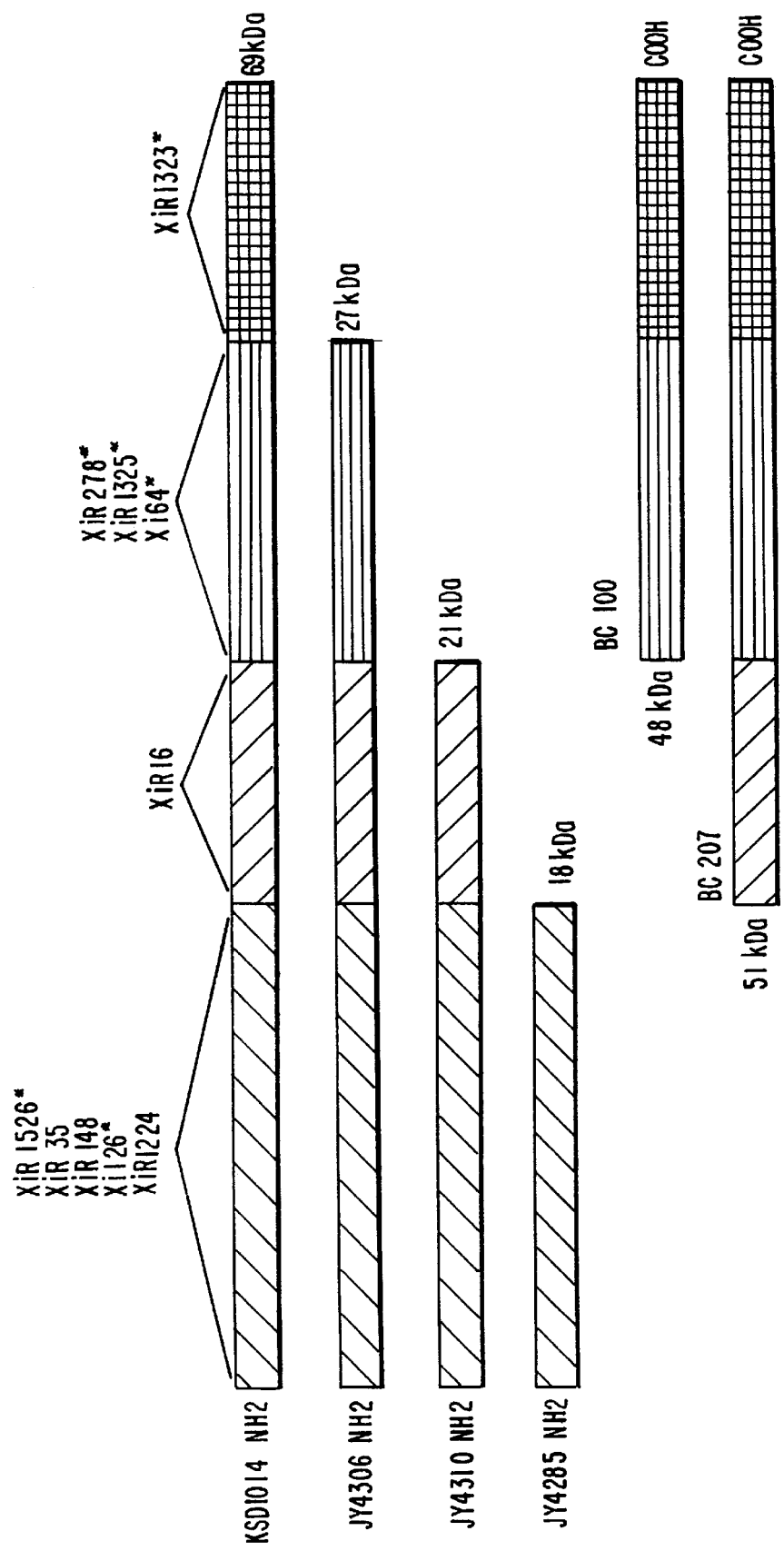

DNA ENCODING A TRUNCATED PNEUMOGOCCAL SURFACE PROTEIN (PSPA)

REFERENCE TO RELATED APPLICATION

This application is continuation of application Ser. No. 07/835,698, filed Feb. 12, 1992, now abandoned, which is a continuation-in-part of copending U.S. patent application Ser. No. 656,773 filed Feb. 15, 1991, now abandoned.

FIELD OF INVENTION

The present invention is concerned with the development of an improved vaccine against pneumococcal infections.

BACKGROUND TO THE INVENTION

*Streptococcus pneumoniae* is an important cause of otitis media, meningitis, bacteremia and pneumonia. Despite the use of antibiotics and vaccines, the prevalence of pneumococcal infections has declined little over the last twenty-five years.

It is generally accepted that immunity to *Streptococcus oneumoniae* can be mediated by specific antibodies against the polysaccharide capsule of the pneumococcus. However, neonates and young children fail to make an immune response against polysaccharide antigens and can have repeated infections involving the same capsular serotype.

One approach to immunizing infants against a number of encapsulated bacteria is to conjugate the capsular polysaccharide antigens to protein to make them immunogenic. This approach has been successful, for example, with *Haemophilus influenzae b* (see U.S. Pat. No. 4,496,538 to Gordon and U.S. Pat. No. 4,673,574 to Anderson). However, there are over eighty known capsular serotypes of *S. pneumoniae* of which twenty-three account for most of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

In McDaniel et al (I), J.Exp.Med. 160:386–397, 1984, there is described the production of hybridoma antibodies that recognize cell surface polypeptide(s) on *S. pneumoniae* and protection of mice from infection with certain strains of encapsulated pneumococci by such antibodies. This surface protein antigen has been termed "pneumococcal surface protein A" or PspA for short.

In McDaniel et al (II), Microbial Pathogenesis 1:519–531, 1986, there are described studies on the characterization of the PspA. Considerable diversity in the PspA molecule in different strains was found, as were differences in the epitopes recognized by different antibodies.

In McDaniel et al (III), J.Exp.Med. 165:381–394, 1987, there is disclosed that immunization of X-linked immunodeficient (XID) mice with non-encapsulated pneumococci expressing PspA, but not isogenic pneumococci lacking PspA, protects mice from subsequent fatal infection with pneumococci.

In McDaniel et al (IV), Infect. Immun., 59:222–228, 1991, there is described immunization of mice with a recombinant full length fragment of PspA that is able to elicit protection against pneumococcal strains of capsular types 6A and 3.

In Crain et al, Infect.Immun., 56:3293–3299, 1990, there is described a rabbit antiserum that detects PspA in 100% (n=95) of clinical and laboratory isolates of strains of *S. pneumoniae*. When reacted with seven monoclonal antibodies to PspA, fifty-seven *S. pneumoniae* isolates exhibited thirty-one different patterns of reactivity.

The PspA protein type is independent of capsular type. It would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with a partially purified PspA from a recombinant λ gt11 clone, elicited protection against challenge with several *S. pneumoniae* strains representing different capsular and PspA types, as described in McDaniel et al (IV), Infect. Immun. 59:222–228, 1991. Although clones expressing PspA were constructed according to that paper, the product was insoluble and isolation from cell fragments following lysis was not possible.

While the protein is variable in structure between different pneumococcal strains, numerous cross-reactions exist between all PspA's, suggesting that sufficient common epitopes may be present to allow a single PspA or at least a small number of PspA's to elicit protection against a large number of *S. pneumoniae* strains.

In addition to the published literature specifically referred to above, the inventors, in conjunction with co-workers, have published further details concerning PspA's, as follows:

1. Abstracts of 89th Annual Meeting of the American Society for Microbiology, p. 125, item D-257, May 1989;
2. Abstracts of 90th Annual Meeting of the American Society for Microbiology, p. 98, item D-106, May 1990;
3. Abstracts of 3rd International ASM Conference on Streptococcal Genetics, p. 11, item 12, June 1990;
4. Talkington et al, Infect. Immun. 59:1285–1289, 1991;
5. Yother et al, J. Bacteriol. 174:601–609, 1992; and
6. Yother et al, J. Bacteriol. 174:610–618, 1992. The latter three publications occurred after the filing of the aforesaid U.S. Ser. No. 656,773.

In the specification which follows and the drawings accompanying the same, there are utilized certain accepted abbreviations with respect to the amino acids represented thereby. The following Table I identifies those abbreviations:

TABLE I

AMINO ACID ABBREVIATIONS

| | |
|---|---|
| A = Ala = Alanine | M = Met = Methionine |
| C = Cys = Cysteine | N = Asn = Asparagine |
| D = Asp = Aspartic Acid | P = Pro = Proline |
| E = Glu = Glutamic Acid | Q = Gln = Glutamine |
| F = Phe = Phenylalanine | R = Arg = Arginine |
| G = Gly = Glycine | S = Ser = Serine |

TABLE I-continued

AMINO ACID ABBREVIATIONS

| H = His = Histidine | T = Thr = Threonine |
|---|---|
| I = Ile = Isoleucine | V = Val = Valine |
| K = Lys = Lysine | W = Try = Tryptophan |
| L = Leu = Leucine | Y = Tyr = Tyrosine |

SUMMARY OF INVENTION

The present invention relates to the preparation of mutants of *S. pneumaniae* that secrete an immunogenic truncated form of the PspA protein, and isolation and purification of the secreted protein. The truncated form of the PspA protein is immunoprotective and contains the protective epitopes of PspA. The PspA protein is soluble in physiologic solution and lacking at least the functional cell membrane anchor region.

BRIEF DESCRIPTION OF DRAWINGS

FIG. 1 is a schematic representation of the domains of the mature PspA;

FIG. 2 is the N-terminal amino acid sequence of PspA (see SEQ ID NO.3), wherein bold upper case letters denote charged hydrophilic amino acids, lower-case letters designate apolar, hydrophobic residues, and underlined bold lower case letters denote uncharged, polar, hydrophilic residues;

FIG. 3A-B is the DNA sequence of the pSpA gene (see SEQ ID NO.1) with deduced amino acid sequence for the PspA protein (see SEQ ID NO.2);

FIG. 4A-B depicts the restriction map of pspA (FIG. 4A) and the use of insertion-duplication mutagenesis to construct mutations in the pSpA gene (FIG. 4B), FIG. 5 shows the deduced amino acid sequence for the N-terminal region of PspA (see SEQ ID NO.4) and the general location of epitopes recognized by monoclonal antibodies;

FIG. 6 shows antibody reactivity with PspA fragments produced by various pspa gene segments; and FIG. 7 shows the mapped location of epitopes in the PspA fragments produced by the different pSpA gene segments.

GENERAL DESCRIPTION OF INVENTION

According to one aspect of the present invention, there is provided a purified immunoprotective pneumacoccal surface protein, comprising a truncated form of PspA which contains the immunoprotective epitopes of the protein and up to about 90% of the whole PspA protein and from which the functional cell membrane anchor region is absent.

Through the technique of insertion-duplication mutagenesis of the psna gene of the strain Rx1 of *Streptococcus pneumoniae* with plasmids containing cloned fragments of the pspA structural gene, it has been possible to produce soluble fragments of PspA that are secreted by pneumococci.

In another aspect of the present invention, therefore, there is provided a method of forming an immunoprotective truncated PspA protein, which comprises effecting insertion-duplication mutagenesis of a bacterium with a pspA gene resulting in the coding of a truncated expressible PspA protein, growing the mutated bacterium to effect expression of a truncated PspA protein, and isolating the protein.

The molecular size of the purified truncated PspA protein obtained may be varied by directing the point of insertion, which determines the termination of gene expression, to different points in the pspA gene. For example, an N-terminal fragment of apparent molecular weight of 43 kD, constituting approximately one-half of the native protein, has been found useful.

The truncated segment which is produced by this procedure is capable of eliciting protection in mice from fatal challenge with type 3 *S. pneumoniael*, demonstrating for the first time that a purified PspA can elicit protection and that this truncated segment of the protein contains protective epitopes of PspA.

Amino acid sequence information was obtained on the N-terminal 45 amino acids of the truncated segment of PspA. This sequence is shown in FIG. 2 SEQ ID NO:3. Predictive secondary structural analysis shows that this sequence has a very strong alpha-helical formation, with no non-helical inserts. About 51% of the segment is composed only of two amino acids, namely lysine, a charged amino acid, and alanine, a non-polar amino acid.

Analysis of this 45-amino acid sequence also reveals that it contains a seven-residue periodicity (see FIG. 2) SEQ ID NO:3. In PspA, the periodicity begins with residue 8 and extends throughout the entire sequence, for nearly eleven turns of the helix. Positions “a” and “d” are occupied by apolar amino acids and position “b”, “c” and “f” generally contain hydrophilic amino acids. Position “f” is predominantly occupied by lysine. Having regard to these observations, this region of PspA is very likely in an alpha-helical coiled-coil configuration. The deduced amino acid sequence for the whole of the $\alpha$-helical coiled-coil region is shown in FIG. 5 SEQ ID NO:4.

We also have cloned and sequenced the entire coding region of pspA (see FIG. 3A-B) SEQ ID NO:1. The deduced amino acid sequence for the PspA protein reveals three distinct regions of the PspA molecule, shown schematically in FIG. 1. Accordingly, a further aspect of the present invention, there is provided a biologically-pure recombinant DNA molecule coding for the PspA protein or portions thereof and having a coding sequence included within set forth in FIG. 3 SEQ ID NO:1or having substantial homology thereto.

The DNA sequence of the pspA gene is contained on a HindIII - KpnI fragment that is 2086 base pairs in length. The pspA gene itself represents approximately 1985 base pairs of this fragment, and comprises an initial region containing transcription and translational signals with translation starting at the ATG/met (nucleotide position 127, codon position −31), followed by a leader sequence extending from the AAG/met (nucleotide position 127, codon position −31) to CGA/ala (nucleotide position 217, codon −1). Mature Pspa starts with the glu amino acid at nucleotide position 220 (codon +1) and ends at the translational stop TAA/OCH at nucleotide position 1984. This translational stop cadon is followed by transcription termination signals.

The amino terminal of the protein sequence, predicted from the DNA sequence of FIG. 3A-B SEQ ID NO:2, contains a 31 amino acid leader sequence and a 45 amino acid sequence identical to the 45 amino acid sequence of the N-terminal of PspA (FIG. 2 SEQ ID NO:3). The amino end of the predicted protein sequence is highly charged and $\alpha$-helical in nature. This region has homology with tropomyosin at the amino acid level (approximately 22% identity and 50% similarity). This homology is due largely to a repeating seven residue periodicity where the first and fourth amino acids are hydrophobic, the intervening amino acids are helix-promoting and the seventh amino acid is charged. This pattern is consistent with that of an α-helical coiled-coil molecule and indicates that the α-helical coil extends through the N-terminal half of the molecule. The amino acid sequence of the whole of the α-helical coil region is shown in FIG. 5 SEQ ID NO:4.

Following the charged helical region is a proline-rich region in which 23 of 81 amino acids are prolines. Immediately carboxy to the proline-rich region is the first of ten highly homologous twenty amino acid repeats. The only significantly hydrophobic region in the sequenced portion of the molecule begins at the last repeat. This potential membrane-spanning region contains several charged amino acids preceding the translational stop codon.

The insertionally-inactivated mutants of *S. pneumoniae* lacking the C-terminal anchor regions are capable of growth in chemically-defined medium and secrete the N-terminal portion of the PspA protein into the medium. The N-terminal region of PspA is highly soluble in the culture medium and is much easier to isolate than the entire molecule. Soluble truncated molecules have been produced using insertional duplicational mutagenesis directed by the cloned PspA DNA fragments shown in FIG. 4A-B. Expression of the same truncated construct (with the pneumococcal promoter) in *E.coli* results in the same PspA fragment being secreted into the periplasm of *E.coli*. PspA is readily released from the periplasm by hypotonic lysis.

Truncated PspA is isolated from culture medium of mutant pneumococci in any convenient manner, such as by tangential flow filtration. Ion-exchange chromatography then is performed on an anionic resin to purify the protein. In this procedure, the solution containing PspA is dialyzed to pH6 in 0.02 M salt solution and passed over the resin. The PspA is eluted from the resin with a gradient of 0.08 to 2.0 M ionic strength and is collected in the fraction between 0.34 and 0.87 M ionic strength, depending on the nature of the column used.

The PspA may be further purified by sodium dodecyl sulfate polyacrylamide gel (SDS-PAGE) electrophoresis. The PspA-containing portion of the gel is identified by staining of the gel and PspA is electroeluted from this portion.

The electrophoresis purification is convenient when only small quantities of PspA are being handled. As an alternative, more suited to large-scale production, the protein may be purified by size chromatography in a pH7 phosphate buffer.

Since it is possible to obtain expression of the truncated form of PspA into the culture medium, as opposed to it being trapped within the cell wall and making purification much more complicated, it is possible to isolate other proteins that have been cloned into the truncated pspA gene by making fusion proteins between pspA and other proteins. Such a technique may be employed to enhance the immunogenicity or preserve the immunogenic structural conformation or presentation of the gene product, to permit the fusion protein to be used in immunization, which may be systemic and/or mucosal, against disease.

One example of such a fusion protein is a fusion of the soluble N-terminal region of PspA and the B-subunit of cholera toxin. Fusion proteins also may be formed by chemical attachment of the truncated PspA protein to other proteins.

Another aspect of the present invention, therefore, provides a method for the production of cloned proteins, which comprises fusing a pspA gene coding for a truncated form of PspA protein with the gene coding for another protein to form a fusion protein clone, transforming *S.pneumoniae*, *E.coli* or other bacteria with the fusion protein clone, growing the transformed bacterium to effect expression of a fusion protein comprising truncated PspA and the other protein into the culture medium, and isolating the fusion protein.

By using this technique, there can be produced cloned proteins in gram positive bacteria, such as pneumococci, for example, *S.pneumoniae*, and mycobacteria, for example, Bacille Calmette-Guerin (BCG). This approach overcomes the problems inherent in the production of proteins in gram negative bacteria, such as *E. coli*, usually used for cloning, in particular the need to purify the recombinant proteins from endotoxin and the toxicity of many gram positive DNA sequences in gram negative organisms.

For the expression of a fusion protein comprising the soluble N-terminal region of PspA and the B-subunit of cholera toxin (CTB), a gene fusion of a pspA gene coding for a truncated form of PspA protein with a ctxB gene coding for the B-subunit of cholera toxin is effected. Following expression of the fusion protein, the PspA and CTB may be cleaved one from another by dilute acid at an asparagine-proline sequence, known to be labile to dilute acid, engineered at the fusion site of the two proteins.

CTB is known to be highly specific for monosinlaganglioside ($G_{M1}$). Accordingly, the fusion PspA-CTB protein may be isolated from the culture medium by adsorption to a $G_{M1}$ affinity column, from which the fusion protein subsequently may be eluted at low pH.

The PspA-CTB fusion protein finds considerable utility in solid phase immunoadsorbant assays. By using the fusion protein, it is possible to coat solid supports, such as microtitration plates, with PspA fragments without having first to isolate the PspA fragments. This may be done by adding bacterial extract containing the fusion protein to plates coated with $G_{M1}$. The PspA-CTB fusion protein then binds to $G_{M1}$ through the CTB moiety, thereby coating the solid support with PspA. The resulting coated product then may be used in a solid phase immunoadsorbant assay for the detection of PspA antibody and/or antigen in test samples. Such immunoadsorbant assays constitute an additional aspect of this invention.

The PspA attachment/anchor region, containing the proline-rich region, the repeat region and/or the C-terminus of PspA, also may be employed to effect expression of heterologous proteins in pneumocacci, or other gram positive or gram negative bacteria in the which the attachment/anchor region is functional. Generally, expression is effected on bacterial membrane, cell walls or cell surfaces in gram positive bacteria and in the periplasm of gram negative bacteria. An example of such heterologous protein is the B-subunit of cholera toxin.

As mentioned above, the truncated form of PspA provided herein contains the immunoprotective epitopes of the protein and hence is useful in a vaccine against pneumococcal infection. Accordingly, a yet further aspect of the present invention provides a vaccine against pneumococcal infection comprising, as an immunogenically-active component, the purified immunoprotective pneumococcal surf ace protein provided herein. The PspA protein may be employed as one component of a multicamponent vaccine which is effective in providing protection from a variety of infections.

In addition, gram positive bacteria which have been transformed to express the pspA gene coding for the truncated soluble PspA protein may be employed, in a live-attenuated or killed form, as an immunologically-active component of a vaccine against pneumococcal infection. In the transformed bacterium, such pspA gene may be fused to a gene coding for another protein. Accordingly, an additional aspect of this invention provides a vaccine against pneumococcal infection comprising, as an immunologically-active component, a live-attenuated or killed bacteria containing a gene coding for the truncated form of PspA.

The truncated form of PspA also may be employed in conjugates with normally weakly-immunogenic or non-immunogenic protection-eliciting molecules, such as various polysaccharides, to achieve immunogenic potentiation thereof. An additional aspect of the invention, therefore, provides a vaccine comprising, as an immunogenically-active component, a conjugate of the purified immunoprotective pneumococcal surface protein provided herein and a normally weakly-immunogenic or non-immunogenic protection-eliciting molecule.

Conserved sequences of pspA, particularly those in the proline-rich and/or repeat regions of the gene, may be employed as probes to detect the presence of pneumococci of various strains, through detection of pneumococcal DNA, in tissues, body fluids and/or secretions. Similarly, portions of the pspA gene may be used in diagnostic kits for the detection of pneumococcal infections.

In addition, primers made based on conserved sequences of pspA, particularly those in the proline-rich and/or repeat regions, may be used to assay for the presence of pneumococci in tissues, body fluids and/or secretions, through amplification of pneumococcal DNA. In this regard, a single primer pair derived from the nucleotide sequence of the pspa gene of S.pneumoniae may be employed in an assay using the polymerase chain reaction (PCR) for the specific detection of Streptococcus pneumoniae.

Specific amplification has been achieved of a 678 base pair DNA fragment from S.pneumoniae strain Rx1. After 30 cycles of amplification, the amplimer was detectable by agarose gel electrophoresis. The fragment was successfully amplified in all 32 strains of S.Pneumoniae tested. PCR DNA amplification was able to detect less than an estimated 20 ficograms total genomic pneumococcal DNA.

Figure 3A:
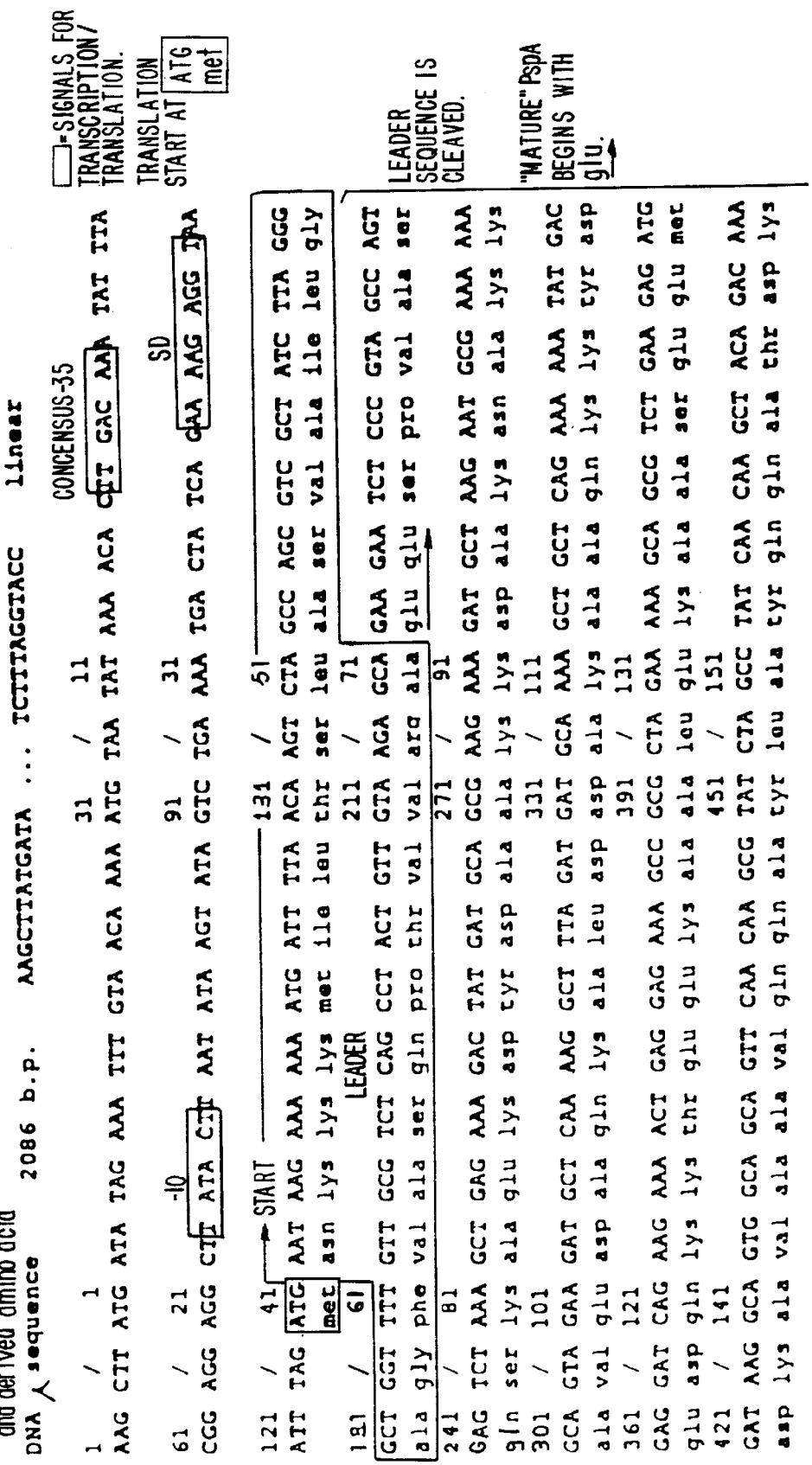

Primers LSM1 and LSM2, having the nucleotide sequences:

LSM1 5'-CCGGATCCAGCTCCTGCACCAAAAC-3' (see SEQ ID NO.5)
LSM2 5' -GCGCTGCGACGGCTTAAACCCATTCA-CCATTGG-3' (see SEQ ID NO.6)

amplified the 678 base pair product from pspA from nucleotides 1312 to 1990 of the Rx1 pspA sequence (FIG. 3A-B).

The PCR analysis using the primers described herein is performed in accordance with conventional PCR techniques, such as are described in the literature, for example, as described in Arnhem et al at C&EN Special Report, 36, Oct. 1, 1990. For detection purposes, the primer may be labelled or labelled nucleotide triphosphates may be included in the PCR reaction to label the PCR amplification product.

The PCR primers may be prepared by well-known methods, for example, by oligonucleotide synthesis or by fragmentation of a larger nucleotide sequence using suitable restriction enzymes.

The ability to use a single primer capable of detecting a large number of S.pneumoniae strains enables a universal PCR detection kit to be provided which is able to diagnose pneumococcal infection in mammals, including humans, independent of the strain which has caused the disease.

EXAMPLES

Example 1

This Example illustrates the preparation and growth of novel strains of S. pneumoniae.

The S. pneumoniae strain Rx1, which is a non-encapsulated derivative of capsular type 2 strain D39 (National Collection of Type Cultures, London, NCTC #7466), was subjected to insertional inactivation (as described in McDaniel et al (III) 1987, Crain et al 1990, Talkington et al 1991, with 10 different cloned fragments of PspA (see FIG. 4A-B). These fragments have all been obtained from restriction digests of cloned PspA DNA on a plasmid in E.coli strain JY4313 (deposited with the American Type Culture Collection on Jan. 31, 1991 under ATCC accession number 68529). This insertional duplication mutagenesis (see FIG. 4A-B) results in the termination of gene expression near the 3' end of the cloned fragment.

One of the resultant strains, JY2008 (deposited with the American Type Culture Collection on Jan. 24, 1991 under accession number 55143), which was produced by a fragment of DNA encoded in pKSD300 (McDaniel et al (III) 1987), produces a PspA fragment of 27 kDa (apparent molecular weight 43 kDa) . This fragment is approximately 40% the size of the native 65 kDa (84 kDa apparent size) protein.

The expected molecular size is based on the deduced amino acid sequence and the apparent molecular size is based on migration in SDS-PAGE. The difference between expected and apparent molecular size is due to the conformation of the PspA fragment.

The proline and repeats/anchor regions (see FIG. 1) were deleted and the resulting protein was unable to attach to cell due to their absence. The unattached protein then may be isolated from culture supernatants, as described below.

By directing the insertion to different points in the PspA gene, different lengths of truncated, non-attached PspA protein derivatives can be produced, as seen in FIG. 7.

STRAINS, PLASMIDS AND PROBES

In the Examples which follow as well as in the accompanying drawings, reference is made to certain plasmids and bacterial strains transformed by such plasmids as well as vector DNA segments, some of which have been deposited with American Type Culture Collection (ATCC), 12301 Parklawn Drive, Rockville Md. 20852 and all of which are fully described herein. The following Table II provides a summary of such materials.

TABLE II

| Identification | Type | Description | Deposit | Location |
|---|---|---|---|---|
| JY4313 | E. coli strain | PspA DNA | ATCC 68529 | Example 1 |
| JY2008 | S. pneumomiae strain | PspA fragment 43 kDa | ATCC 55143 | Example 1 |

TABLE II-continued

| Identification | Type | Description | Deposit | Location |
|---|---|---|---|---|
| JY4306 | E. coli strain | PspA fragment 43 kDa | ATCC 68522 | Example 3 |
| JY4310 | | PspA fragment 21 kDa | None | FIG. 7 |
| JY4285 | | PspA fragment 18 kDa | None | FIG. 7 |
| pJY4163 | Plasmid | Expression plasmid used for expression of PspA -CTB fusion protein (29 kDa) | None | Example 6 |
| JY4323 | DNA probe | HindIII-KpaI segment | None | Example 9 |
| JY4306 | DNA probe | HindIII-Dra-I segment | None | Example 9 |
| JY4262 | DNA probe | BclI-Bst-NI segment | None | Example 9 |

The pneumococcal strain JY2008 was grown in 6 liters of a chemically defined medium (see Inf. Imm. 27:444) supplemented with 0.10% choline chloride, 0.075% L-cysteine hydrochloride and 0.25% $NaHCO_3$. The supernatant fluid of the mid-log phase culture of JY2008 was harvested using a 0.22 μm membrane tangential flow filter and concentrated 60 fold.

Introduction of the plasmid pKSD300 into the unmodified D39 strain similarly yielded the 43 kD lo truncated PspA protein. Introduction of the plasmid pKSD300 into the type 3 S.pneumoniae strain WU2 (PspA protein approximately 92 kD) yielded, upon growth of the organism, a non-attached truncated PspA protein of approximately 46 kD molecule size.

Example 2

This Example illustrates the purification of PspA.

The concentrated supernatant fluid, produced as described in Example 1, was washed in 0.1 M PBS, pH 7.2, and ultracentrifuged at 196,000 xg. The supernatant fluid was diluted 1:5 in 20 mM L-histidine buffer-NaCl, the pH adjusted to 6.0 and the injected into a DEAE-fibered Isonet-D2 an ion exchange column.

A stepwise NaCl gradient from 80 mM to 2 M was applied to the column and PspA-containing fractions (0.32 to 0.64 M ionic strength) were pooled and separated on an SDS-polyacrylamide gel. The proteins on a representative section of the gel were stained with comassie Blue R-250 to identify PspA. The fraction containing PspA was excised from the remainder of the SDS-gel and electroeluted from the excised gel. The eluted protein was precipitated in a 50:50 metha-nol:acetone solvent and resuspended in PBS. Purity of product was confirmed by silver staining and Western Immunoblotting with mAb Xi126 (IgG 2b, k, see McDaniel et al (I), supra).

Example 3

This Example illustrates the isolation of PspA from the periplasmic space of Escherichia coli.

Isolation from the periplasmic space of E. coli was accomplished by standard techniques. E. coli strain JY4306 (which produces the 43 kDa N-terminal fragment of PspA, the amino acid sequence of which is shown in FIG. 3 SEQ ID NO:2. This strain was deposited with ATCC on Jan. 31, 1991 under accession number 68522) was washed in buffered saline, incubated in 20% sucrose, 10 mM EDTA, 25 mM Tris pH 7.7 for 10 minutes at 0° C. The cells then were spun at 400 xg for 10 minutes at 0° C. All supernatant was removed from the pellet and the pellet was resuspended rapidly in about 100 volumes of 4° C. water. After 10 minutes the suspension was centrifuged at 4,000 xg for 10 minutes at 4° C. The pellet was discarded and the supernatant, which contained the PspA was saved. Concentration of the supernatant was by standard procedures such as concentration against solid sucrose or ultrafiltration. Purification of the protein isolated from E. coli proceeded by the same chromatography techniques used for the isolated of the 43 kDa (truncated) PspA from the media of growing pneumococci.

Example 4

This Example illustrates the immunogenic properties of the PspA protein.

Sixteen 7-week old CBA/N mice carrying the Xid mutation (Jackson Laboratories, Bar Harbor, Me.) were bled via the periorbital sinus to establish pre-exposure levels of antibody to PspA. Purified PspA, prepared as described in Example 2, was emulsified in complete Freund's adjuvant and injected subcutaneously into the inguinal and axillary regions, delivering approximately 5 μg of protein per mouse. Fourteen days later, the mice were injected intraperitoneally with 5 μg of PspA, prepared as described in Example 2. Control mice were immunized via the same routes with sterile SDS buffer. Seven days after the last immunization, all mice were bled via the periorbital sinus and were challenged intravenously with 300 CFU of the type 3 strain WU2, grown as described in Example 1.

Preimmunization and prechallenge sera were analyzed by Western immunoblots to establish baseline and postimmunization response to the truncated protein. The PspA of strain WU2 was electrophoresed and transferred to nitrocellulose membranes. The membranes were separated into strips and probed with the appropriate mouse antisera at a 1:50 dilution for 2 hours, incubated with biotinylated goat anti-mouse immunoglobulin for 1 hr. washed and incubated with Strepavidin-conjugated phosphatase. The membranes were developed with 5-bromo-4-chloro-3-indoyl phosphate toludine salt with 0.01% into blue tetrazolium.

Of the eight CBA/N mice immunized with the purified fragment of PspA, all were still alive 14 days after challenge with strain WU2 and none showed any signs of illness following challenge. Of the eight mice immunized with buffer controls, six were dead by two days post challenge, while the two remaining control mice appeared very sick, with ruffled fur, arched back and decreased movement, two to three days following challenge but survived. chi-square analysis indicated that there was a significant difference ($P<0.003$) in survival between the immunized and control groups.

Preimmunization and prechallenge sera were analyzed by Western immunoblotting. None of the preimmunization sera contained antibody to truncated PSpA. Postimmunization sera from eight of eight mice contained detectable antibodies to PspA, and six mice had very strong anti-PspA reactions. When the challenge strain WU2 was probed with the antisera, all the immunized mice had antibodies that were highly cross-reactive with the WU2 PspA epitopes. No control mice developed antibodies to PspA.

The immunization data is summarized in the following Table III:

TABLE III

| Immunogen | Detection of Antibody to PspA | Alive at 2 days post challenge | Alive at 14 days post challenge |
|---|---|---|---|
| Isolated PspA (Example 2) | 8/8 | 8/8 | 8/8 |
| Sterile SDS (control) | 0/8 | 2/8 | 2/8 |

As may be seen from the data in Table III, immunization with two 5 μg doses of the purified PspA molecule elicited protection against fatal infection of CBA/N mice and elicited antibodies reactive with the PspA of the challenge strain.

Example 5

This Example illustrates sequencing of the PspA protein.

Purified PspA, prepared as described in Example 2, was electrophoresed through 9% resolving gels containing recrystallized SDS with the Laemmli buffer system (Nature 227:680). The gels were soaked twice in a 10 mM 3-(cyclohexylamino)-i-propanesulfonic acid, pH 11.0, containing 10% methanol for 10 minutes. A polyvinylidene difluoride membrane (PVDF) was wetted completely for several seconds in 100% methanol, then washed in CAPS buffer for 10 min. PspA was electrotransferred to the PVDF membrane in CAPS buffer at 0.5 A f or 1 hr. After transfer, the membrane was washed two times in deionized water for 5 min, and stained with 0.1% Coomassie Blue R-250 in 50% methanol for 20 minutes. The section of the membrane containing PspA was excised and destained in 40% methanol and 10% acetic acid for 5 min. The membrane was cut into small segments and stored in sterile Eppendorf tubes until sequencing.

The isolated PspA was sequenced directly from the PVDF membranes. FIG. 2 SEQ ID NO:3 depicts the N-terminal 45 residue amino acid sequence and FIG. 5 depicts the amino acid sequence for the whole alpha-helical region. The DNA sequence of the whole pspA gene and the deduced amino acid sequence for the PspA protein are shown in FIG. 3A-B SEQ ID NO:2.

Example 6

This Example illustrates the use of the PSPA 5'-sequence and/or the PspA N-terminal region to serve as an expression and leader sequence for expressing and/or excreting/ secreting heterologous proteins from S.pneumoniae and E.coli. In this Example, there is described the expression of the N-terminal of the PspA protein fused to the B-subunit of cholera toxin (CTB) through a genetic fusion and the excretion of the fused protein from pneumococci and its secretion into the periplasmic space of E.coli.

A fusion protein consisting of CTB and the N-terminal half of PspA was constructed and expressed in E.coli. The HindIII/DraI pspA gene fragment used contained all the pspA transcription and translation initiation signals and the PspA signal peptide leader sequence for transport across the cell membrane. The mature PspA encoded by this fragment is predicted to be a product of 29 kDa (observed molecular weight of 42 kDa), encompassing more than 90% of the α-hemical coiled-coil domain. The CTB fragment used lacked transcription and translation initiation signals. Expression from pspA promoter through pspA and then in-frame translational readthrough into the CTB-encoding gene ctxB resulted in production of a 12 kDa CTB product fused to the upstream PspA product. The PspA-CTB fusion protein was stably expressed in both high and low copy number plasmids (pUC18, more than 100 copies/cell; pJY4163, about 15 to 30 copies/cell) in E.coli.

The fusion products were of the expected size (about 54 kDa) and reacted with antibody to both PspA and CTB. That the CTB product retained its functionality was demonstrated by the ability of the fusion protein to bind ganglioside $GM_1$, a property of CTB.

The high level of expression of the fusion product apparently resulted in a reduced rate of processing and/or conformational changes that prevented the protein from being completely transported to the periplasm. However, in the lower copy number construct, about 60% of the fusion protein was localized in the periplasm, where large quantities were readily released from E. coli by osmotic shock.

In addition to expression in E.coli, the fusion protein also was expressed in S.pneumoniae by transformation of the low copy number construct into the avirulent S.pneumaniae Rx1 to generate an insertion-duplication mutant. In this way, the gene encoding the fusion protein was integrated into the S.pneumoniae chromosome, from which it was stably expressed. As in the case of Example 1, the truncated PspA molecule lacking the attachment/anchor region, this time in the form of the PspA-CTB fusion protein, was excreted into the culture supernatant. The fusion protein product was of the expected molecular size (54 kDa), reacted with antibody to PspA and CTB, and bound $G_{M1}$.

Example 7

This Example illustrates the use of PspA attachment or anchor region to permit expression of heterologous proteins on the surface of S.pneumoniae or other bacteria in which the attachment/anchor sequence is functional in particular the expression of a PspA-CTB (cholera toxin B subunit) fusion expressed on the surface of pneumococci.

The N-terminal encoding region of PspA, including its transcription and translation initiation signals and its signal peptide leader sequence, is linked via a translationally in-frame genetic fusion to the CTB-encoding ctxB fragment that lacks transcription and translation initiation and termination signals. This sequence is followed in-frame by the PspA attachment/anchor domain, including part or all of the proline, repeat and C-terminal domains. The resulting fusion protein is directed to the outside of the cell via the PspA leader sequence, which is cleaned following transport across the membrane, and then attached to cell by the PspA attachment/anchor sequence. The heterologous protein, located between the two PspA fragments is expressed on the outside surface of the membrane and, in *S.pneumoniae*, on the surface of the cell.

Example 8

This Example illustrates the expression of truncated and full length PspA by the *Mycobacterium tuberculosis* strain Bacille Calmette-Guerin (BCG).

BCG was chromosomally modified to incorporate the pspA gene coding for the truncated PspA protein. The 43 kDa truncated PspA protein was expressed from the modified BCG to approximately 15% of total BCG protein. This result was achieved with an expression vector construct carrying the pspA gene segment encoding the 43 kDa region without its 5'-secretion signal. Expression was only about 1% of BCG(3 protein when the PspA or mycobacterial signal sequences were included. In either case, a significant portion of the expressed PspA was excreted into the medium. Expression of the 43 kDa PspA protein in a fusion with the mycobacterial lipoprotein signal sequence resulted in the expression of the recombinant PspA in the membrane fraction of BCG.

This latter result suggested that the fusion of the lipoprotein signal sequence resulted in acylation of the recombinant PspA. Fluorescent activated cell sorting with fluorochrome-conjugated monoclonal antibodies to PspA demonstrated expression of PspA on the surface of these bacteria.

Example 9

This Example illustrates the close homology of portions of the pspA gene among different strains of pneumococci and the potential that such homology may be useful for molecular (DNA) approaches to detect pneumococci in tissues, body fluids and/or secretions and to identify pneumococci grown from patient samples.

Three DNA probes were employed, namely full length pspA, JY4323 (N-terminal HindIII to C-terminal KpnI) , the N-terminal half of pspA, JY4306 (N-terminal HindIII to DraI at position 996 (see FIG. 3 SEQ ID NO:1) and most of the proline and repeat regions, JY4262 (BclI at position 1221 to BstNI at position 1832). Under stringency conditions requiring 95% identity, probes JY4323 and JY4262 reacted with cells of over 200 independent isolates of *S.pneumoniae* by Southern blot.

When the chromosomal DNA was cut with HindIII, there generally was observed that each of these probes detected two discrete bands whose exact size was dependent on the strain examined. In Rx1 pneumococci, the two bands were 4.0 and 9. 1 kb. The 4.0 kb band corresponded to pspA and was altered or absent in PspA mutants. The other band shares some homology with the coding regions for both the N-terminal and C-terminal halves of PspA but is not affected by pspA mutations. The JY4323 and JY4262 probes failed to react with another gram positive bacterium, *Streptococcus pyogenes*, and a gram negative bacterium, *Salmonella typhimurium*. The N-terminal probe, JY4306, recognized about one-third of the strains of pneumococci tested.

These results indicate that a sequence included in the proline/repeat region is shared by all strains of pneumococci and apparently not by other bacterial species. Sequences in the N-terminal half of the molecule appear to be more variable.

Example 10

This Example illustrates the detection and determination of the location of epitopes in the α-helical N-terminal region of PspA.

Monoclonal antibodies protective against pneumococcal infection in a mouse model, denoted by an asterisk in FIGS. 5, 6 and 7, were used to determine the location of epitopes for each antibody in the α-helical N-terminal region of PspA. The sites were mapped to fragments of PspA. The results are illustrated in FIGS. 5 to 7, with FIG. 5 showing the deduced amino acid sequence for the N-terminal region of PspA and the general location of epitopes recognized by monoclonal antibodies, FIG. 6 showing antibody reactivity with PspA fragments produced by various pspA gene segments, and FIG. 7 showing the mapped location of epitopes in the PspA fragments produced by the different pspA gene segments.

Numbers 138, 193 and 261 in FIG. 5 indicate break positions in the PspA fragments used to map the location of epitopes detected by monoclonal antibodies Xi1526, Xi126, XiR35, XiR38, XiR1224, XiR16, Xi64, XiR278, Xi1325 and Xi1323. The asterisk (*) after some of the antibodies denotes those which are able to protect against fatal pneumococcal infection with strain WU2 pneumococci.

In addition, the vertical lines to the right of the Figure indicate those areas predicted to have coiled-coil α-helical structure. The divisions to the left of the Figure indicate the mapped location of the epitopes for each antibody.

SUMMARY OF DISCLOSURE

In summary of this disclosure, the present invention relates to a truncated PspA molecule capable of eliciting an immunoprotective response and hence containing the protective epitopes of PspA protein. Modifications are possible within the scope of this invention.

SEQUENCE LISTINGS

Submitted with this application are Sequence Listings, identified as follows:

(a) SEQ ID No: 1 shows the nucleotide sequence and derived amino acid sequence for the HindIII-KpnI fragment containing the complete pspa gene, as shown in FIG. 3.

(b) SEQ ID No: 2 shows the derived amino acid sequence for the PspA protein, as shown in FIG. 3.

(c) SEQ ID No: 3 shows the N-terminal amino acid sequence of PspA, as shown in FIG. 2.

(d) SEQ ID No: 4 shows the derived amino acid sequence for the N-terminal region of PspA as shown in FIG. 5.

(e) SEQ ID No: 5 shows the nucleotide sequence for primer LSM1.

(f) SEQ ID No: 6 shows the nucleotide sequence for primer LSM2.

What we claim is:

1. An isolated DNA molecule consisting of a nuclaotide sequence coding for an immunoprotective pneumococcal surface protein A (PspA) wherein said PspA comprises the sequence of FIG. 3 (SEQ ID NO: 2).

2. An isolated DNA molecule consisting of a nucleotide sequence coding for an α-helical coiled coil region of pneumocaccal surface protein A (PspA) wherein said PspA comprises the sequence of FIG. 3 (SEQ ID NO: 2).

3. An isolated DNA molecule consisting of a nucleotide sequence coding for a proline rich region and repeat region of pneumococcal surface protein A (PspA) wherein said PspA comprises the sequence of FIG. 3 (SEQ ID NO: 2).

4. An isolated DNA molecule consisting of a nucleotide sequence coding for a truncated form of whole pneumccoccal surface protein A (PspA) wherein said whole PspA comprises the sequence of FIG. 3 (SEQ ID NO: 2), wherein said truncated PspA contains immunoprotective epitopes and has the cell membrane anchor region absent therefrom.

5. An isolated DNA molecule consisting of a nucleotide sequence coding for a truncated form of whole pneumococcal surface protein A (PspA) wherein said whole PspA comprises the sequence of FIG. 3 (SEQ ID NO: 2) wherein said truncated PspA contains about 50% of the whole PspA protein and has the cell membrane anchor region, the repeats region, and the proline region absent therefrom.

6. An isolated DNA molecule consisting of a nucleotide sequence coding for a truncated form of whole pneumococcal surface protein A (PspA) said whole PspA comprises the sequence of FIG. 3 (SEQ ID NO: 2), wherein said truncated PspA contains immunoprotective epitopes and about 90% of the whole PspA protein and has the cell anchor region absent therefrom.

7. A method for forming an immunoprotective truncated pneumococcal surface protein A (PspA), which comprises:

incorporating a vector comprising the isolated DNA molecule of claim 4 into a bacterium by transformation whereby said transformed bacterium expresses said DNA molecule, growing said bacterium to effect expression of said truncated PspA protein, and isolating said truncated PspA protein.

8. The method of claim 7 wherein said transformed bacterium is a *Stretococcus pneumoniae* strain, said strain is grown in a defined medium to effect expression of the truncated PspA protein into said medium, and the truncated PspA protein is isolated from the medium.

9. The method of claim 8 wherein said mutated strain is *Streptococcus pneumoniae 1 strain JY2008* (ATCC Accession No. 55143).

10. The method of claim 7 wherein said transformed bacterium is a *Eschoricha coli* strain, said strain is grown to effect expression of the truncated PspA protein into the proplasm of said strain, and the truncated PspA protein is isolated from the periplasm of said strain.

11. The method of claim 10 wherein said strain is *Escherichia coli* strain JY4306 (ATCC Accession No. 68522).

12. The method of claim 7 wherein said isolated truncated PspA protein is purified by ion-exchange chromatography.

13. The method of claim 7 wherein said tranformed bacterium is selected from the group consisting of *Streptococcus pneumoniae* and *Escherichia coli*.

* * * * *

UNITED STATES PATENT AND TRADEMARK OFFICE
CERTIFICATE OF CORRECTION

PATENT NO. : 5,965,400

DATED : October 12, 1999

INVENTOR(s) : BRILES ET AL.

It is certified that error appears in the above-identified patent and that said Letters Patent is hereby corrected as shown below:

ON THE COVER PAGE:

[54] Please change "DNA ENCODING A TRUNCATED PNEUMOGOCCAL SURFACE PROTEIN (PspA)" to --DNA ENCODING A TRUNCATED PNEUMOCOCCAL SURFACE PROTEIN (PspA)--.

Signed and Sealed this

Twenty-third Day of May, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO.    : 5,965,400
DATED         : October 12, 1999
INVENTOR(S)   : Briles et al.

It is certified that error appears in the above-identified patent and that said Letters Patent is hereby corrected as shown below:

In the Drawings delete Figure 3 and insert substitute Figure 3 (enclosed).

Signed and Sealed this

Twenty-sixth Day of February, 2002

Attest:

JAMES E. ROGAN
*Attesting Officer*     *Director of the United States Patent and Trademark Office*

FIG. 3A

PspA - sequence -> 1-phase Translation
and derived amino acid
DNA λ sequence    2086 b.p.    AAGCTTATGATA ... TCTTAGGTACC    linear

```
                                                                              CONSENSUS-35
  1    /         1           11           21           31           41           51
  AAG  CTT  ATG  ATA  TAG  AAA  TTT  GTA  ACA  AAA  TAA  TAT  AAA  ACA  CTT  GAC  AAA  TAT  TTA
                                                                                      SD
 61    /        21           31           41           51           61           71
  CGG  AGG  AGG  CTT  AAT  ATA  AGT  ATA  GTC  AAA  TGA  CTA  TCA  GAA  AAG  AGG  TAA
                                              ──── START ────                  ─10─
121    /        41           51           61           71           81           91
  ATT  TAG  ATG  AAT  AAG  AAA  AAA  GAC  ATT  TTA  ACA  AGT  CTA  TAA  AGC  AGG  GTC  GCT  TTA
                 met  asn  lys  lys  lys  asp  ile  leu  thr  ser  leu  ala  ser  val  ala  leu
                                         LEADER
181    /        61           71           81           91          101          111
  GCT  GCT  TTT  GTT  GTT  GCG  TCT  CAG  GCT  GAT  GTT  GTA  AGA  GCA  GAA  GTC  GCT  ATC  TTA
  ala  gly  phe  val  val  ala  ser  gln  ala  asp  val  val  arg  ala  glu  val  ala  ile  leu
                                                               LEADER SEQUENCE IS CLEAVED.
241    /        81           91          101          111          121          131
  GAG  TCT  AAA  GCT  GAG  AAA  GAC  TAT  GAT  GCA  GCG  AAG  AAA  GAT  GCT  CAG  AAA  AAA
  glu  ser  lys  ala  glu  lys  asp  tyr  asp  ala  ala  lys  lys  asp  ala  gln  lys  lys
                                                                  "NATURE" PspA BEGINS WITH glu.
301    /       101          111          121          131          141          151
  GIN  TCT  AAA  GCT  GAG  AAA  GAC  TAT  GAT  GCA  GCG  AAG  AAA  GAT  GCT  CAG  AAA  AAA
  gln  ser  lys  ala  glu  lys  asp  tyr  asp  ala  ala  lys  lys  asp  ala  gln  lys  lys 361    /       121          131          141          151          161          171
  GCA  GTA  GAA  GAT  GCT  CAA  AAG  GCT  TTA  GAT  GAT  GCA  AAA  GCT  GCA  GAA  AAA  TAT  GAC
  ala  val  glu  asp  ala  gln  lys  ala  leu  asp  asp  ala  lys  ala  ala  glu  lys  tyr  asp 421    /       141
  GAC  GAT  CAG  AAG  ACT  GAG  GAG  AAA  GCC  CTA  GAA  GCA  GCT  TCT  GAA  ATG
  asp  asp  gln  lys  thr  glu  glu  lys  ala  leu  glu  ala  ala  ser  glu  met 481    /       161
  GAG  GAT  CAG  AAG  ACT  GAG  GAG  AAA  GCC  CTA  GAA  GCA  GCT  TCT  GAA  ATG
  glu  asp  gln  lys  thr  glu  glu  lys  ala  leu  glu  ala  ala  ser  glu  met 541    /
  GAT  AAG  GCA  GTG  GCA  ACT  GTT  CAA  CAA  TAT  CTA  GCC  TAT  CAA  CAA  CAA  GCT  ACA  GAC
  asp  lys  ala  val  ala  thr  val  gln  gln  tyr  leu  ala  tyr  gln  gln  gln  ala  thr  asp 601    /
  GAT  AAG  GCA  GTG  GCA  ACT  GTT  CAA  CAA  TAT  CTA  GCC  TAT  CAA  CAA  CAA  GCT  ACA  GAC
  asp  lys  ala  val  ala  val  ala  ala  val  tyr  gln  ala  tyr  gln  ala  thr  ala  thr  asp asp  lys  ala  val  ala  val  ala  ala  val  tyr  gln  ala  tyr  gln  ala  thr  asp  lys
```

☐ = SIGNALS FOR TRANSCRIPTION/TRANSLATION.

TRANSLATION START AT ATG met.

FIG. 3B

```
481  /   161
GCC  GCA  AAA  GAC  GCA  GCA  GAT  AAG  ATG  ATA  GAT  GCT  AAG  AAA  CGC  GAA  GAG  GCA
ala  ala  lys  asp  ala  ala  asp  lys  met  ile  asp  ala  lys  lys  arg  glu  glu  ala
541  /   181                                     511  /   171
AAA  ACT  AAA  TTT  ACT  GTT  CGA  GTT  CCT  GTA  GTT  CCT  GAG  AAA  AAA  TTC  GCT  GAG
lys  thr  lys  phe  asn  thr  val  arg  ala  val  pro  glu  lys  lys  arg  glu  ala  glu
601  /   201                                     571  /   191
ACT  AAG  AAA  AAA  TCA  GAA  GAA  GCT  AAA  CAA  AAA  CCA  GAG  CTT  ACT  AAA  CTA  GAA
thr  lys  lys  lys  ser  glu  glu  ala  lys  gln  lys  pro  glu  leu  thr  lys  leu  glu
661  /   221                                     631  /   211
GAA  GCT  AAA  AAA  TTA  GAA  GAG  GAA  AAA  AAA  GCA  CCA  GAA  CTT  ACT  AAA  AAA  GTC
glu  ala  lys  lys  leu  glu  glu  glu  lys  lys  ala  pro  glu  leu  thr  lys  lys  val
721  /   241                                     691  /   231
CAT  GAA  GAA  GTC  GCT  CCT  CAA  ATC  GCT  GAA  ATG  GCT  ACT  GAA  AAT  CAA  GTT  AGA
asp  glu  glu  val  ala  pro  gln  ile  ala  glu  met  ala  thr  glu  asn  gln  val  arg
781  /   261                                     751  /   251
CTA  GAA  CAA  GAG  CTC  AAA  GAG  ATT  GAT  CAG  TCT  CAA  TCA  GAA  GAT  TAT  CCT  CAT
leu  glu  gln  glu  leu  lys  glu  ile  asp  gln  ser  gln  ser  glu  asp  tyr  ala  his
841  /   281                                     811  /   271
TTC  CCT  CCT  CTT  CAA  TCT  AAA  TTG  GAT  CCC  AAA  AAA  GCT  AAA  CTA  AAA  CTT  GAA
phe  arg  pro  leu  gln  ser  lys  leu  asp  ala  lys  lys  ala  lys  leu  lys  leu  glu
901  /   301                                     871  /   291
GAG  TTA  AGT  GAT  AAG  ATT  GAT  GAG  TTA  GAC  GCT  GAA  ATT  GCA  AAA  CTT  CAA  GGT
glu  leu  ser  asp  lys  ile  asp  glu  leu  asp  ala  glu  ile  ala  lys  leu  gln  gly
961  /   321                                     931  /   311
AAA  GCT  GAA  GAA  AAC  AAT  CTA  GAA  GAC  TAC  TTT  AAA  GAA  GGT  TTA  GAG  AAA  ACT
lys  ala  ala  ala  glu  glu  asn  asn  val  glu  asp  tyr  phe  lys  lys  glu  gly  lys  thr
                                                 991  /   331
```

FIRST 45 aa, BEGINNING WITH glu, ARE SAME AS FOUND BY aa SEQUENCING (TALKINGTON ETC.)

α-HELICAL, CHARGED DOMAIN

FIG. 3C

```
1021 /  341
ATT GCT AAA GCT GAA TTA GAA AAA GCT GAC CTT AAG AAA GCA GTT AAT
ile  ala  lys  ala  glu  leu  glu  lys  ala  asp  leu  lys  lys  ala  val  asn
1081 /  361
GAG CCA AAA CCA GCT CCA GAA ACT CCA GCC CCA CCA GCT GAA CAA
glu  pro  lys  pro  ala  pro  glu  thr  pro  ala  pro  pro  ala  glu  gln
1141 /  381
CCA AAA CCA GCG CCT CAA CCA GCT CCT AAA CCA GAG AAG CCA GCT GAA
pro  lys  pro  ala  pro  gln  pro  ala  pro  lys  pro  glu  lys  pro  ala  glu
1201 /  401
CAA CCA AAA CCA GAA ACA GAT CAA GAT CAA CCA GCT CCA CCT CGT AGA TCA
gln  pro  lys  pro  glu  thr  asp  gln  asp  gln  pro  ala  pro  arg  arg  ser
1261 /  421
GAA GAA TAT AAT CGC TTG ACT CAA CAG CAA CCG AAA GCT GAA AAA CCA GCT CCT
glu  glu  tyr  asn  arg  leu  thr  gln  gln  gln  pro  lys  ala  glu  lys  pro  ala  pro
1321 /  441
GCA CCA AAA ACA GGC TGG AAA CAA GAA GGT ATG TGG TAC TTC TAC AAT ACT GAT GGT
ala  pro  lys  thr  gly  trp  lys  gln  glu  gly  met  trp  tyr  phe  tyr  asn  thr  asp  gly
1381 /  461
TCA ATG GCG ACA GGA TGG CTC CAA AAC GGT TCA TGG TAC TAC CTC AAC AGC AAT GGT
ser  met  ala  thr  gly  trp  leu  gln  asn  gly  ser  trp  tyr  tyr  leu  asn  ser  asn  gly
1441 /  481
GCT ATG GCT ACA GGT TGG CTC CAA TAC GGT TCA TGG TAC TAC CTC AAC AAC AAC GGC
ala  met  ala  thr  gly  trp  leu  gln  tyr  gly  ser  trp  tyr  tyr  leu  asn  asn  asn  gly
1501 /  501
GCT ATG GCA ACA GGT TGG GCT AAA GTC AAC GGT TCA TGG TAC TAC CTC AAC AAT GGT
ala  met  ala  thr  gly  trp  ala  lys  val  asn  gly  ser  trp  tyr  tyr  leu  asn  asn  gly
1561 /  521
GCT ATG GCT ACA GGT TGG CTC CAA TAC AAC GGT TCA TGG TAT TAC CTC AAC GCT GGC
ala  met  ala  thr  gly  trp  leu  gln  tyr  asn  gly  ser  trp  tyr  tyr  leu  asn  ala  gly
```

PROLINES

PROLINE-RICH DOMAIN

FIG. 3D

```
1621 /   541
GCT ATG GCA ACA GGT TGG GCT AAA GTC AAC TGG TCA TAC TAC CTC AAC GCT AAT GGT
ala met ala thr gly trp ala lys val asn trp ser tyr tyr leu asn ala asn gly
                                                            1651 /   551
GCT ATG GCT ACA GGT TGG CTC CAA TAC AAC GGT TAC TYR CTC AAC GCT AAC GGT
ala met ala thr gly trp leu gln tyr asn gly tyr tyr leu asn ala asn gly
1681 /   561                                                1711 /   571
GCT ATG GCT ACA GGT TGG AAA TAC AAC GGT TAC TYR CTC AAC GCT AAC GGT
ala met ala thr gly trp lys tyr asn gly tyr tyr leu asn ala asn gly
1741 /   581                                                1771 /   591
GCT ATG GCT ACA GGT TGG GCT AAA GTC AAC GGT TAC TYR CTC AAC GCT AAT GGT
ala met ala thr gly trp ala lys val asn gly tyr tyr leu asn ala asn gly
1801 /   601                                                1831 /   611
GCT ATG GCA ACA GGT TGG GTC AAA GAT GGA CAT ACC TGG TAT CTT GAA AAC GCA GCT
ala met ala thr gly trp val lys asp gly his thr trp tyr leu glu asn ala ala
1861 /   621                                                1891 /   631
GCT ATG AAA GCA AGC CAA TGG TTC AAA GTA TCA GAT AAA TGG TAC TAT GTC AAT TTA
ala met lys ala ser gln trp phe lys val ser asp lys trp tyr tyr val asn leu
1921 /   641                                                1951 /   651
GCT GCC CTT GCA AAC ACA ACT GTA GAT GCC TAT AAA GTC TGG AAT GCC GAA GGT TGG ─┐ TAIL
ala ala leu ala asn thr thr val asp ala tyr lys val trp asn ala glu gly trp │
1981 /   661                                                2011 /   671
GTT GCC GAT TAA ATT AAA TTC ACA CAT TTC ACA TTT AAT TTT TGA AAC AAA           ─┘
val ala asp OCH ile lys ala cys OCH glu his leu thr phe asn ala asn gly lys
2041 /   681                                                2071 /   691
GAT AAG GTT CGA TTG AGA TTT ATG TTC GTA TTC TTT AGG TAC
asp lys val arg leu asn arg phe met phe val phe phe arg tyr
```
TRANSLATION STOP (END) IS AT TAA OCH

REPEAT DOMAIN

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 2085 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (B) STRAIN: Streptococcus pneumoniae Rx1

(vii) IMMEDIATE SOURCE:
      (B) CLONE: JY2008

(ix) FEATURE:
      (A) NAME/KEY: intron
      (B) LOCATION: 1..2085

(ix) FEATURE:
      (A) NAME/KEY: CDS
      (B) LOCATION: join(127..1983, 1987..1992, 1996..2007, 2011
         ..2025, 2029..2031, 2035..2085)

(xi) SEQUENCE DESCRIPTION: SEQ ID NO:1:

```
AAGCTTATGA TATAGAAATT TGTAACAAAA ATGTAATATA AAACACTTGA CAAATATTTA      60

CGGAGGAGGC TTATACTTAA TATAAGTATA GTCTGAAAAT GACTATCAGA AAGAGGTAA      120

ATTTAG ATG AAT AAG AAA AAA ATG ATT TTA ACA AGT CTA GCC AGC GTC        168
       Met Asn Lys Lys Lys Met Ile Leu Thr Ser Leu Ala Ser Val
        1               5                  10

GCT ATC TTA GGG GCT GGT TTT GTT GCG TCT CAG CCT ACT GTT GTA AGA       216
Ala Ile Leu Gly Ala Gly Phe Val Ala Ser Gln Pro Thr Val Val Arg
 15                  20                  25                  30

GCA GAA GAA TCT CCC GTA GCC AGT CAG TCT AAA GCT GAG AAA GAC TAT       264
Ala Glu Glu Ser Pro Val Ala Ser Gln Ser Lys Ala Glu Lys Asp Tyr
                 35                  40                  45

GAT GCA GCG AAG AAA GAT GCT AAG AAT GCG AAA AAA GCA GTA GAA GAT       312
Asp Ala Ala Lys Lys Asp Ala Lys Asn Ala Lys Lys Ala Val Glu Asp
             50                  55                  60

GCT CAA AAG GCT TTA GAT GAT GCA AAA GCT GCT CAG AAA AAA TAT GAC       360
Ala Gln Lys Ala Leu Asp Asp Ala Lys Ala Ala Gln Lys Lys Tyr Asp
         65                  70                  75

GAG GAT CAG AAG AAA ACT GAG GAG AAA GCC GCG CTA GAA AAA GCA GCG       408
Glu Asp Gln Lys Lys Thr Glu Glu Lys Ala Ala Leu Glu Lys Ala Ala
     80                  85                  90

TCT GAA GAG ATG GAT AAG GCA GTG GCA GCA GTT CAA CAA GCG TAT CTA       456
Ser Glu Glu Met Asp Lys Ala Val Ala Ala Val Gln Gln Ala Tyr Leu
 95                 100                 105                 110

GCC TAT CAA CAA GCT ACA GAC AAA GCC GCA AAA GAC GCA GCA GAT AAG       504
Ala Tyr Gln Gln Ala Thr Asp Lys Ala Ala Lys Asp Ala Ala Asp Lys
                115                 120                 125

ATG ATA GAT GAA GCT AAG AAA CGC GAA GAA GAG GCA AAA ACT AAA TTT       552
Met Ile Asp Glu Ala Lys Lys Arg Glu Glu Glu Ala Lys Thr Lys Phe
            130                 135                 140

AAT ACT GTT CGA GCA ATG GTA GTT CCT GAG CCA GAG CAG TTG GCT GAG       600
```

```
                Asn Thr Val Arg Ala Met Val Val Pro Glu Pro Glu Gln Leu Ala Glu
                            145                 150                 155

ACT AAG AAA AAA TCA GAA GAA GCT AAA CAA AAA GCA CCA GAA CTT ACT              648
Thr Lys Lys Lys Ser Glu Glu Ala Lys Gln Lys Ala Pro Glu Leu Thr
        160                 165                 170

AAA AAA CTA GAA GAA GCT AAA GCA AAA TTA GAA GAG GCT GAG AAA AAA              696
Lys Lys Leu Glu Glu Ala Lys Ala Lys Leu Glu Glu Ala Glu Lys Lys
175                 180                 185                 190

GCT ACT GAA GCC AAA CAA AAA GTG GAT GCT GAA GAA GTC GCT CCT CAA              744
Ala Thr Glu Ala Lys Gln Lys Val Asp Ala Glu Glu Val Ala Pro Gln
                195                 200                 205

GCT AAA ATC GCT GAA TTG GAA AAT CAA GTT CAT AGA CTA GAA CAA GAG              792
Ala Lys Ile Ala Glu Leu Glu Asn Gln Val His Arg Leu Glu Gln Glu
                210                 215                 220

CTC AAA GAG ATT GAT GAG TCT GAA TCA GAA GAT TAT GCT AAA GAA GGT              840
Leu Lys Glu Ile Asp Glu Ser Glu Ser Glu Asp Tyr Ala Lys Glu Gly
                225                 230                 235

TTC CGT GCT CCT CTT CAA TCT AAA TTG GAT GCC AAA AAA GCT AAA CTA              888
Phe Arg Ala Pro Leu Gln Ser Lys Leu Asp Ala Lys Lys Ala Lys Leu
        240                 245                 250

TCA AAA CTT GAA GAG TTA AGT GAT AAG ATT GAT GAG TTA GAC GCT GAA              936
Ser Lys Leu Glu Glu Leu Ser Asp Lys Ile Asp Glu Leu Asp Ala Glu
255                 260                 265                 270

ATT GCA AAA CTT GAA GAT CAA CTT AAA GCT GCT GAA GAA AAC AAT AAT              984
Ile Ala Lys Leu Glu Asp Gln Leu Lys Ala Ala Glu Glu Asn Asn Asn
                275                 280                 285

GTA GAA GAC TAC TTT AAA GAA GGT TTA GAG AAA ACT ATT GCT GCT AAA             1032
Val Glu Asp Tyr Phe Lys Glu Gly Leu Glu Lys Thr Ile Ala Ala Lys
                290                 295                 300

AAA GCT GAA TTA GAA AAA ACT GAA GCT GAC CTT AAG AAA GCA GTT AAT             1080
Lys Ala Glu Leu Glu Lys Thr Glu Ala Asp Leu Lys Lys Ala Val Asn
        305                 310                 315

GAG CCA GAA AAA CCA GCT CCA GCT CCA GAA ACT CCA GCC CCA GAA GCA             1128
Glu Pro Glu Lys Pro Ala Pro Ala Pro Glu Thr Pro Ala Pro Glu Ala
        320                 325                 330

CCA GCT GAA CAA CCA AAA CCA GCG CCG GCT CCT CAA CCA GCT CCC GCA             1176
Pro Ala Glu Gln Pro Lys Pro Ala Pro Gln Pro Ala Pro Ala
335                 340                 345                 350

CCA AAA CCA GAG AAG CCA GCT GAA CAA CCA AAA CCA GAA AAA ACA GAT             1224
Pro Lys Pro Glu Lys Pro Ala Glu Gln Pro Lys Pro Glu Lys Thr Asp
                355                 360                 365

GAT CAA CAA GCT GAA GAA GAC TAT GCT CGT AGA TCA GAA GAA GAA TAT             1272
Asp Gln Gln Ala Glu Glu Asp Tyr Ala Arg Arg Ser Glu Glu Glu Tyr
                370                 375                 380

AAT CGC TTG ACT CAA CAG CAA CCG CCA AAA GCT GAA AAA CCA GCT CCT             1320
Asn Arg Leu Thr Gln Gln Gln Pro Pro Lys Ala Glu Lys Pro Ala Pro
        385                 390                 395

GCA CCA AAA ACA GGC TGG AAA CAA GAA AAC GGT ATG TGG TAC TTC TAC             1368
Ala Pro Lys Thr Gly Trp Lys Gln Glu Asn Gly Met Trp Tyr Phe Tyr
400                 405                 410

AAT ACT GAT GGT TCA ATG GCG ACA GGA TGG CTC CAA AAC AAC GGT TCA             1416
Asn Thr Asp Gly Ser Met Ala Thr Gly Trp Leu Gln Asn Asn Gly Ser
415                 420                 425                 430

TGG TAC TAC CTC AAC AGC AAT GGT GCT ATG GCT ACA GGT TGG CTC CAA             1464
Trp Tyr Tyr Leu Asn Ser Asn Gly Ala Met Ala Thr Gly Trp Leu Gln
                435                 440                 445

TAC AAT GGT TCA TGG TAT TAC CTC AAC GCT AAC GGC GCT ATG GCA ACA             1512
Tyr Asn Gly Ser Trp Tyr Tyr Leu Asn Ala Asn Gly Ala Met Ala Thr
                450                 455                 460

GGT TGG GCT AAA GTC AAC GGT TCA TGG TAC TAC CTC AAC GCT AAT GGT             1560
```

```
Gly Trp Ala Lys Val Asn Gly Ser Trp Tyr Tyr Leu Asn Ala Asn Gly
        465                 470                 475

GCT ATG GCT ACA GGT TGG CTC CAA TAC AAC GGT TCA TGG TAT TAC CTC         1608
Ala Met Ala Thr Gly Trp Leu Gln Tyr Asn Gly Ser Trp Tyr Tyr Leu
        480                 485                 490

AAC GCT AAC GGC GCT ATG GCA ACA GGT TGG GCT AAA GTC AAC GGT TCA         1656
Asn Ala Asn Gly Ala Met Ala Thr Gly Trp Ala Lys Val Asn Gly Ser
495                 500                 505                 510

TGG TAC TAC CTC AAC GCT AAT GGT GCT ATG GCT ACA GGT TGG CTC CAA         1704
Trp Tyr Tyr Leu Asn Ala Asn Gly Ala Met Ala Thr Gly Trp Leu Gln
                515                 520                 525

TAC AAC GGT TCA TGG TAC TAC CTC AAC GCT AAC GGT GCT ATG GCT ACA         1752
Tyr Asn Gly Ser Trp Tyr Tyr Leu Asn Ala Asn Gly Ala Met Ala Thr
            530                 535                 540

GGT TGG GCT AAA GTC AAC GGT TCA TGG TAC TAC CTC AAC GCT AAT GGT         1800
Gly Trp Ala Lys Val Asn Gly Ser Trp Tyr Tyr Leu Asn Ala Asn Gly
        545                 550                 555

GCT ATG GCA ACA GGT TGG GTG AAA GAT GGA GAT ACC TGG TAC TAT CTT         1848
Ala Met Ala Thr Gly Trp Val Lys Asp Gly Asp Thr Trp Tyr Tyr Leu
        560                 565                 570

GAA GCA TCA GGT GCT ATG AAA GCA AGC CAA TGG TTC AAA GTA TCA GAT         1896
Glu Ala Ser Gly Ala Met Lys Ala Ser Gln Trp Phe Lys Val Ser Asp
575                 580                 585                 590

AAA TGG TAC TAT GTC AAT GGT TTA GGT GCC CTT GCA GTC AAC ACA ACT         1944
Lys Trp Tyr Tyr Val Asn Gly Leu Gly Ala Leu Ala Val Asn Thr Thr
                595                 600                 605

GTA GAT GGC TAT AAA GTC AAT GCC AAT GGT GAA TGG GTT TAA GCC GAT         1992
Val Asp Gly Tyr Lys Val Asn Ala Asn Gly Glu Trp Val     Ala Asp
            610                 615                 620

TAA ATT AAA GCA TGT TAA GAA CAT TTG ACA TTT TAA TTT TGA AAC AAA         2040
    Ile Lys Ala Cys     Glu His Leu Thr Phe     Phe     Asn Lys
                625                 630

GAT AAG GTT CGA TTG AAT AGA TTT ATG TTC GTA TTC TTT AGG TAC             2085
Asp Lys Val Arg Leu Asn Arg Phe Met Phe Val Phe Phe Arg Tyr
        635                 640                 645

(2) INFORMATION FOR SEQ ID NO:2:

(i) SEQUENCE CHARACTERISTICS:
        (A) LENGTH: 648 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Lys Lys Met Ile Leu Thr Ser Leu Ala Ser Val Ala Ile
 1               5                  10                  15

Leu Gly Ala Gly Phe Val Ala Ser Gln Pro Thr Val Val Arg Ala Glu
                20                  25                  30

Glu Ser Pro Val Ala Ser Gln Ser Lys Ala Glu Lys Asp Tyr Asp Ala
            35                  40                  45

Ala Lys Lys Asp Ala Lys Asn Ala Lys Lys Ala Val Glu Asp Ala Gln
        50                  55                  60

Lys Ala Leu Asp Asp Ala Lys Ala Ala Gln Lys Tyr Asp Glu Asp
65                  70                  75              80

Gln Lys Lys Thr Glu Glu Lys Ala Ala Leu Glu Lys Ala Ala Ser Glu
                85                  90                  95

Glu Met Asp Lys Ala Val Ala Ala Val Gln Gln Ala Tyr Leu Ala Tyr
                100                 105                 110
```

-continued

```
Gln Gln Ala Thr Asp Lys Ala Ala Lys Asp Ala Ala Asp Lys Met Ile
        115                 120                 125
Asp Glu Ala Lys Lys Arg Glu Glu Ala Lys Thr Lys Phe Asn Thr
130                 135                 140
Val Arg Ala Met Val Val Pro Glu Pro Glu Gln Leu Ala Glu Thr Lys
145                 150                 155                 160
Lys Lys Ser Glu Glu Ala Lys Gln Lys Ala Pro Glu Leu Thr Lys Lys
            165                 170                 175
Leu Glu Glu Ala Lys Ala Lys Leu Glu Glu Ala Glu Lys Lys Ala Thr
            180                 185                 190
Glu Ala Lys Gln Lys Val Asp Ala Glu Glu Val Ala Pro Gln Ala Lys
            195                 200                 205
Ile Ala Glu Leu Glu Asn Gln Val His Arg Leu Glu Gln Glu Leu Lys
210                 215                 220
Glu Ile Asp Glu Ser Glu Ser Glu Asp Tyr Ala Lys Glu Gly Phe Arg
225                 230                 235                 240
Ala Pro Leu Gln Ser Lys Leu Asp Ala Lys Lys Ala Lys Leu Ser Lys
                245                 250                 255
Leu Glu Glu Leu Ser Asp Lys Ile Asp Glu Leu Asp Ala Glu Ile Ala
            260                 265                 270
Lys Leu Glu Asp Gln Leu Lys Ala Ala Glu Glu Asn Asn Asn Val Glu
            275                 280                 285
Asp Tyr Phe Lys Glu Gly Leu Glu Lys Thr Ile Ala Ala Lys Lys Ala
290                 295                 300
Glu Leu Glu Lys Thr Glu Ala Asp Leu Lys Lys Ala Val Asn Glu Pro
305                 310                 315                 320
Glu Lys Pro Ala Pro Ala Pro Glu Thr Pro Ala Pro Glu Ala Pro Ala
                325                 330                 335
Glu Gln Pro Lys Pro Ala Pro Ala Pro Gln Pro Ala Pro Ala Pro Lys
            340                 345                 350
Pro Glu Lys Pro Ala Glu Gln Pro Lys Pro Glu Lys Thr Asp Asp Gln
            355                 360                 365
Gln Ala Glu Glu Asp Tyr Ala Arg Arg Ser Glu Glu Glu Tyr Asn Arg
            370                 375                 380
Leu Thr Gln Gln Gln Pro Pro Lys Ala Glu Lys Pro Ala Pro Ala Pro
385                 390                 395                 400
Lys Thr Gly Trp Lys Gln Glu Asn Gly Met Trp Tyr Phe Tyr Asn Thr
                405                 410                 415
Asp Gly Ser Met Ala Thr Gly Trp Leu Gln Asn Asn Gly Ser Trp Tyr
                420                 425                 430
Tyr Leu Asn Ser Asn Gly Ala Met Ala Thr Gly Trp Leu Gln Tyr Asn
            435                 440                 445
Gly Ser Trp Tyr Tyr Leu Asn Ala Asn Gly Ala Met Ala Thr Gly Trp
450                 455                 460
Ala Lys Val Asn Gly Ser Trp Tyr Leu Asn Ala Asn Gly Ala Met
465                 470                 475                 480
Ala Thr Gly Trp Leu Gln Tyr Asn Gly Ser Trp Tyr Leu Asn Ala
                485                 490                 495
Asn Gly Ala Met Ala Thr Gly Trp Ala Lys Val Asn Gly Ser Trp Tyr
                500                 505                 510
Tyr Leu Asn Ala Asn Gly Ala Met Ala Thr Gly Trp Leu Gln Tyr Asn
            515                 520                 525
Gly Ser Trp Tyr Tyr Leu Asn Ala Asn Gly Ala Met Ala Thr Gly Trp
530                 535                 540
```

-continued

Ala Lys Val Asn Gly Ser Trp Tyr Tyr Leu Asn Ala Asn Gly Ala Met
545             550                 555                 560

Ala Thr Gly Trp Val Lys Asp Gly Asp Thr Trp Tyr Tyr Leu Glu Ala
                565                 570                 575

Ser Gly Ala Met Lys Ala Ser Gln Trp Phe Lys Val Ser Asp Lys Trp
            580                 585                 590

Tyr Tyr Val Asn Gly Leu Gly Ala Leu Ala Val Asn Thr Thr Val Asp
        595                 600                 605

Gly Tyr Lys Val Asn Ala Asn Gly Glu Trp Val Ala Asp Ile Lys Ala
    610                 615                 620

Cys Glu His Leu Thr Phe Phe Asn Lys Asp Lys Val Arg Leu Asn Arg
625                 630                 635                 640

Phe Met Phe Val Phe Phe Arg Tyr
                645

(2) INFORMATION FOR SEQ ID NO:3:

(i) SEQUENCE CHARACTERISTICS:
        (A) LENGTH: 619 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:3:

Met Asn Lys Lys Lys Met Ile Leu Thr Ser Leu Ala Ser Val Ala Ile
1               5                   10                  15

Leu Gly Ala Gly Phe Val Ala Ser Gln Pro Thr Val Val Arg Ala Glu
            20                  25                  30

Glu Ser Pro Val Ala Ser Gln Ser Lys Ala Glu Lys Asp Tyr Asp Ala
        35                  40                  45

Ala Lys Lys Asp Ala Lys Asn Ala Lys Lys Ala Val Glu Asp Ala Gln
    50                  55                  60

Lys Ala Leu Asp Asp Ala Lys Ala Ala Gln Lys Lys Tyr Asp Glu Asp
65                  70                  75                  80

Gln Lys Lys Thr Glu Glu Lys Ala Ala Leu Glu Lys Ala Ala Ser Glu
                85                  90                  95

Glu Met Asp Lys Ala Val Ala Ala Val Gln Gln Ala Tyr Leu Ala Tyr
            100                 105                 110

Gln Gln Ala Thr Asp Lys Ala Ala Lys Asp Ala Ala Lys Met Ile
            115                 120                 125

Asp Glu Ala Lys Lys Arg Glu Glu Ala Lys Thr Lys Phe Asn Thr
130                 135                 140

Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
                165                 170                 175

Leu Glu Glu Ala Lys Ala Lys Leu Glu Glu Ala Glu Lys Lys Ala Thr
            180                 185                 190

Glu Ala Lys Gln Lys Val Asp Ala Glu Glu Val Ala Pro Gln Ala Lys
        195                 200                 205

Ile Ala Glu Leu Glu Asn Gln Val His Arg Leu Glu Gln Glu Leu Lys
    210                 215                 220

Glu Ile Asp Glu Ser Glu Ser Glu Asp Tyr Ala Lys Glu Gly Phe Arg
225                 230                 235                 240

```
Ala Pro Leu Gln Ser Lys Leu Asp Ala Lys Ala Lys Leu Ser Lys
            245                 250                 255

Leu Glu Glu Leu Ser Asp Lys Ile Asp Glu Leu Asp Ala Glu Ile Ala
            260                 265                 270

Lys Leu Glu Asp Gln Leu Lys Ala Glu Glu Asn Asn Asn Val Glu
            275                 280                 285

Asp Tyr Phe Lys Glu Gly Leu Glu Lys Thr Ile Ala Ala Lys Lys Ala
    290                 295                 300

Glu Leu Glu Lys Thr Glu Ala Asp Leu Lys Lys Ala Val Asn Glu Pro
305                 310                 315                 320

Glu Lys Pro Ala Pro Ala Pro Glu Thr Pro Ala Pro Glu Ala Pro Ala
                325                 330                 335

Glu Gln Pro Lys Pro Ala Pro Ala Pro Gln Pro Ala Pro Ala Pro Lys
            340                 345                 350

Pro Glu Lys Pro Ala Glu Gln Pro Lys Pro Glu Lys Thr Asp Asp Gln
    355                 360                 365

Gln Ala Glu Glu Asp Tyr Ala Arg Arg Ser Glu Glu Tyr Asn Arg
    370                 375                 380

Leu Thr Gln Gln Gln Pro Pro Lys Ala Glu Lys Pro Ala Pro Ala Pro
385                 390                 395                 400

Lys Thr Gly Trp Lys Gln Glu Asn Gly Met Trp Tyr Phe Tyr Asn Thr
                405                 410                 415

Asp Gly Ser Met Ala Thr Gly Trp Leu Gln Asn Asn Gly Ser Trp Tyr
            420                 425                 430

Tyr Leu Asn Ser Asn Gly Ala Met Ala Thr Gly Trp Leu Gln Tyr Asn
            435                 440                 445

Gly Ser Trp Tyr Tyr Leu Asn Ala Asn Gly Ala Met Ala Thr Gly Trp
    450                 455                 460

Ala Lys Val Asn Gly Ser Trp Tyr Tyr Leu Asn Ala Asn Gly Ala Met
465                 470                 475                 480

Ala Thr Gly Trp Leu Gln Tyr Asn Gly Ser Trp Tyr Tyr Leu Asn Ala
            485                 490                 495

Asn Gly Ala Met Ala Thr Gly Trp Ala Lys Val Asn Gly Ser Trp Tyr
            500                 505                 510

Tyr Leu Asn Ala Asn Gly Ala Met Ala Thr Gly Trp Leu Gln Tyr Asn
            515                 520                 525

Gly Ser Trp Tyr Tyr Leu Asn Ala Asn Gly Ala Met Ala Thr Gly Trp
    530                 535                 540

Ala Lys Val Asn Gly Ser Trp Tyr Tyr Leu Asn Ala Asn Gly Ala Met
545                 550                 555                 560

Ala Thr Gly Trp Val Lys Asp Gly Asp Thr Trp Tyr Tyr Leu Glu Ala
            565                 570                 575

Ser Gly Ala Met Lys Ala Ser Gln Trp Phe Lys Val Ser Asp Lys Trp
            580                 585                 590

Tyr Tyr Val Asn Gly Leu Gly Ala Leu Ala Val Asn Thr Thr Val Asp
    595                 600                 605

Gly Tyr Lys Val Asn Ala Asn Gly Glu Trp Val
    610                 615
```

(2) INFORMATION FOR SEQ ID NO:4:

(i) SEQUENCE CHARACTERISTICS:
        (A) LENGTH: 45 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:4:

```
Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys
                35                  40                  45
```

(2) INFORMATION FOR SEQ ID NO:5:

(i) SEQUENCE CHARACTERISTICS:
        (A) LENGTH: 289 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:5:

```
Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys Tyr Asp Glu
                35                  40                  45

Asp Gln Lys Lys Thr Glu Glu Lys Ala Ala Leu Glu Lys Ala Ala Ser
            50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
                100                 105                 110

Thr Val Arg Ala Met Val Val Pro Glu Pro Gln Leu Ala Glu Thr
            115                 120                 125

Lys Lys Lys Ser Glu Glu Ala Lys Gln Lys Ala Pro Glu Leu Thr Lys
        130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
                180                 185                 190

Lys Glu Ile Asp Glu Ser Glu Ser Glu Glu Asp Tyr Ala Lys Glu Gly
                195                 200                 205

Phe Arg Ala Pro Leu Gln Ser Lys Leu Asp Ala Lys Lys Ala Lys Leu
        210                 215                 220

Ser Lys Leu Glu Glu Leu Ser Asp Lys Ile Asp Glu Leu Asp Ala Glu
225                 230                 235                 240

Ile Ala Lys Leu Glu Asp Gln Leu Lys Ala Ala Glu Glu Asn Asn Asn
                245                 250                 255

Val Glu Asp Tyr Phe Lys Glu Gly Leu Glu Lys Thr Ile Ala Ala Lys
                260                 265                 270
```

```
Lys Ala Glu Leu Glu Lys Thr Glu Ala Asp Leu Lys Lys Ala Val Asn
    275                 280                 285
Glu
```

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
CCGGATCCAG CTCCTGCACC AAAAAC                                           26
```

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GCGCTGCGAC GGCTTAAACC CATTCACCAT TGG                                   33
```

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:8:

```
Ile Lys Ala Cys
1
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:9:

```
Glu His Leu Thr Phe
1               5
```

(2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: amino acid

```
(xi) SEQUENCE DESCRIPTION: SEQ ID NO:10:

Asn Lys Asp Lys Val Arg Leu Asn Arg Phe Met Phe Val Phe Phe Arg
1               5                   10                  15
Tyr
```